United States Patent
Weinberg et al.

(10) Patent No.: US 8,142,370 B2
(45) Date of Patent: Mar. 27, 2012

(54) ELECTRO-RHEOLOGICAL FLUID BRAKE AND ACTUATOR DEVICES AND ORTHOTIC DEVICES USING THE SAME

(75) Inventors: Brian Weinberg, Brookline, MA (US); Jason Nikitczuk, North Brunswick, NJ (US); Constantinos Mavroidis, Arlington, MA (US)

(73) Assignee: Northeastern University, Boston, MA (US)

( * ) Notice: Subject to any disclaimer, the term of this patent is extended or adjusted under 35 U.S.C. 154(b) by 1357 days.

(21) Appl. No.: 11/667,402

(22) PCT Filed: Nov. 9, 2005

(86) PCT No.: PCT/US2005/040404
§ 371 (c)(1),
(2), (4) Date: May 9, 2007

(87) PCT Pub. No.: WO2006/052954
PCT Pub. Date: May 18, 2006

(65) Prior Publication Data
US 2008/0097269 A1   Apr. 24, 2008

Related U.S. Application Data

(60) Provisional application No. 60/626,256, filed on Nov. 9, 2004, provisional application No. 60/626,365, filed on Nov. 9, 2004.

(51) Int. Cl.
*A61F 5/00* (2006.01)

(52) U.S. Cl. ............... 601/5; 601/23; 601/33; 602/16
(58) Field of Classification Search .............. 601/5, 23, 601/33, 34, 35; 623/26, 43; 602/5, 16, 20, 602/23, 27; 482/5, 8, 111, 115, 118; 188/267.1
See application file for complete search history.

(56) References Cited

U.S. PATENT DOCUMENTS

| | | | |
|---|---|---|---|
| 3,144,921 A | 8/1964 | Martinek et al. | |
| 4,444,298 A | 4/1984 | Stangroom | |
| 4,896,754 A * | 1/1990 | Carlson et al. | 188/267.1 |
| 4,898,266 A | 2/1990 | Garrett et al. | |
| 4,898,267 A | 2/1990 | Garrett et al. | |
| 5,469,947 A | 11/1995 | Anzai et al. | |
| 5,573,088 A | 11/1996 | Daniels | |
| 5,762,584 A | 6/1998 | Daniels | |
| 5,788,618 A * | 8/1998 | Joutras | 482/114 |
| 6,129,690 A | 10/2000 | Hamlin et al. | |
| 6,610,101 B2 | 8/2003 | Herr et al. | |
| 6,966,882 B2 * | 11/2005 | Horst | 601/5 |
| 6,969,365 B2 | 11/2005 | Scorvo | |
| 7,101,487 B2 | 9/2006 | Hsu et al. | |
| 2004/0102723 A1 | 5/2004 | Horst | |

* cited by examiner

*Primary Examiner* — Quang D Thanh
(74) *Attorney, Agent, or Firm* — Weingarten, Schurgin, Gagnebin & Lebovici LLP

(57) ABSTRACT

Electro-rheological fluid brake or actuator devices provide controllable resistance with or without inclusion of active torque output in either direction of rotation under manual or computer control. The brake and actuator devices are suitable for use in an orthotic device for a joint, such as the knee or elbow.

28 Claims, 29 Drawing Sheets

Direction B

ELECTRO-RHEOLOGICAL FLUID BRAKE AND ACTUATOR DEVICES AND ORTHOTIC DEVICES USING THE SAME

CROSS REFERENCE TO RELATED APPLICATIONS

This application claims the benefit under 35 U.S.C. §119 (e) of U.S. Provisional Patent Application No. 60/626,256, filed on Nov. 9, 2004, and U.S. Provisional Patent Application No. 60/626,365, filed Nov. 9, 2004, the disclosures of which are incorporated by reference herein.

STATEMENT REGARDING FEDERALLY SPONSORED RESEARCH OR DEVELOPMENT

N/A

BACKGROUND OF THE INVENTION

Various types of actuators and brakes are known. For instance, a DC motor can be used as an actuator to control output torque. Such motors can be difficult to control for certain applications and may be large and heavy. Increasing the output torque generally requires increasing the size of the motor. DC motors are not ideal in many cases for providing resistive control or braking for these and other reasons. As another example, a friction brake can be used for resistive control but not for providing an output torque. It is disadvantageous in that it generates heat, is subject to wear and reliability problems, and can be harmed by contaminates. Magnetic brakes are known and used for resistive control, but not for providing an output torque. They also generate heat and can be hard to control and provide a "jerky" engagement. The MRF brake similarly is not useful for providing an output torque. It is also subject to excessive heat generation and can be heavy and large. Thus, these known types of actuators can either control output torque or modulate input torque, but none of them can perform both functions.

Rehabilitation of injured joints, such as the knee or elbow, can employ various approaches. In one approach, a passive orthotic device or orthosis is worn externally by an individual to provide constant support or resistance to the joint. In passive orthotic devices, the corrective or bias forces they supply are either constant or not capable of being changed in real time. These orthotic devices are widespread, and their relatively low cost, availability and simplicity have contributed to their usefulness.

Another category of rehabilitative device is able to change the resistance or applied force in real time, usually through some form of electronic control. Some of these devices are wearable and can be described as active orthotic devices. For example, one such device is able to lock the knee's position to avoid hyperextension and limit the range of motion. Another device is able to enhance or assist in mobility via the use of actuators. Generally, these devices are limited to retraining the natural gait motion and to muscle enhancement. These devices tend to be bulky and cumbersome, which hinders their use, and the inclusion of active elements increases the overall size, cost and weight.

The most effective tools for rehabilitation are rehabilitation machines, such as isokinetic and CPM machines. These machines are generally found in physical therapy, athletic training, or research facilities. They provide high resistive and sometimes assistive forces, while providing a unique tailoring of the rehabilitation regime to nearly any individual. Their broad abilities increase their proficiency as a rehabilitation tool.

SUMMARY OF THE INVENTION

The present invention relates to an electro-rheological fluid (ERF) device that combines the control functionality of electro-rheological fluids and the motive capabilities of compact brakes and/or actuators. As used herein, the term "motive" refers to the property of relating to motion or to the causing of motion. The brake or damper device is capable of controllable resistance in either direction of rotation under manual or computer control. The ERF actuator device is capable of active force outputs.

The present invention also relates to an orthotic device that is portable and controllable by a motive device that can provide variable resistance and/or actuating functionalities, utilizing preferably an ERF brake/damper or actuator as described above. In one embodiment, the orthotic ERF brake/damper device according to the invention is compact and lightweight with strong, highly tunable torque capabilities, fully portable and wearable with onboard sensors, power and control circuitry, and real time capabilities for closed loop computer control for optimizing rehabilitation exercises while in use. In a further embodiment, an orthotic device according to the invention includes an actuator as an active feature. Preferably, this orthosis exhibits all the characteristics of the resistive device as well as the additional abilities to force motion of the knee, perform muscle enhancement and provide force feedback.

Thus, in one aspect, the invention is directed to an electro-rheological fluid actuator for generating a torque or force output and for providing resistance to a torque or force input, the actuator including a housing comprising an insulative case, an input/output shaft rotatably mounted in the case; a plurality of rotatable members disposed arcuately within the case and coupled to the shaft; a plurality of rotatable electrodes formed as segments of a cylinder, each electrode mounted to an associated rotatable member for rotation therewith; a cylindrical ground electrode fixed to the case and concentric with the rotatable electrodes, a gap disposed between the ground electrode and the rotatable electrodes; an electro-rheological fluid disposed within the gap; and a plurality of linear actuator elements disposed within an associated rotatable member to actuate rotation of the associated rotatable member. Preferably, the linear actuators are operative sequentially to provide stepwise rotation of the rotatable members and are also operative in conjunction with the rotatable electrodes, wherein rotation of a portion of the electrodes is locked by activation of the electro-rheological fluid and rotation of one rotatable electrode is permitted to provide stepwise rotation of the rotatable members.

Furthermore, the electro-rheological fluid preferably is activatable to provide resistance to an input torque on the shaft via a shear stress on the rotatable electrodes, and the actuator further includes a plurality of rolling contacts operative to bring power to the rotatable electrodes, to the ground electrode and to the linear actuators, wherein the rolling contacts are aligned on an axle extending radially from the shaft, the rolling contacts rollable over contacts on a surface of the rotatable members. More preferably, the actuator further includes a ratcheting mechanism operative to control direction of rotation of the linear actuator elements, wherein the ratcheting mechanism includes a ratchet gear attached to the shaft, the ratchet gear having two rows of opposed teeth, and a ratchet cam operative to engage one row of teeth in a clockwise mode and another row of teeth in a counterclockwise mode or wherein the ratcheting mechanism is operative in a neutral free-wheeling mode. The ratchet cam further can be mounted for pivoting motion by an elastic shaft, the elastic shaft mounted in a cam follower element to cause pivoting of the ratchet cam, the cam follower element can be operative to travel a sinusoidal path activated by an external element to adjust the direction of rotation. The linear actuator elements can include electromagnets, solenoids, piezoelectric actuators and/or electro-active polymers.

In another aspect, the invention is directed to an electro-rheological fluid brake device for providing resistance to a torque or force input, the brake device including a housing comprising an insulative case, a shaft rotatably mounted in the case; one or more rotatable cylindrical electrodes mounted to the shaft for rotation therewith; one or more ground cylindrical electrodes fixed to the case and disposed in opposition to and concentrically with the rotatable electrodes, a gap disposed between the ground electrode and the rotatable electrodes; and an electro-rheological fluid disposed within the gap. Preferably, the rotatable cylindrical electrodes comprise a single integral part and the ground cylindrical electrodes comprise a single integral part.

In another aspect, the invention is directed to an electro-rheological fluid brake device for providing resistance to a torque or force input, the brake device including a housing comprising an insulative case, a shaft rotatably mounted in the case; one or more rotatable electrodes mounted to the shaft for rotation therewith; one or more ground electrodes fixed to the case and disposed in opposition to the rotatable electrodes, a gap disposed between the ground electrode and the rotatable electrodes; the rotatable electrodes comprising circular plates fixed at an inner circumference to a central rotating mount attached to the shaft, the ground electrodes comprising circular plates fixed to inserts at an outer circumference, the rotatable electrodes and ground electrodes interleaved and insertable as a unit into the case; and an electro-rheological fluid disposed within the gap between the ground electrodes and the rotatable electrodes. Preferably, the brake device further includes an alignment mechanism operative to adjust a gap size between the rotating electrodes and the ground electrodes, wherein the alignment mechanism is accessible from an exterior of the case. More preferably, the rotating electrodes are fixed to the central rotating mount with locks that fit within keyed slots on the rotating electrodes.

In a further aspect, the invention is directed to an orthotic device for a joint including a frame removably fixable to a limb of a user, the frame comprising a hinge assembly disposable at a joint of the limb; the electro-rheological actuator described herein; and a gear assembly attached to the shaft of the electro-rheological fluid actuator to couple an input or output force or torque to the hinge assembly. Alternatively, the orthotic device according to the invention can include either of the electro-rheological fluid brake devices described herein. Preferably, an orthotic device according to the invention comprises a knee brace and the frame is configured for attachment to a leg, or alternatively, the orthotic device comprises an elbow brace and the frame is configured for attachment to an arm. More preferably, the orthotic device includes a sensor system comprising a sensor assembly operative to measure angle, velocity, and acceleration of the joint, wherein the sensor assembly is operative to provide closed-loop control of the device. The sensor assembly can also be operative to measure torque on the shaft to provide closed-loop control of the device. Any of the orthotic devices according to the invention can include further a second electro-rheological fluid device disposed on an opposite side of the joint. A preferred orthotic device further includes a controller assembly operative to control the electro-rheological fluid device, wherein the control assembly is operative to provide remote communication. More preferably, the orthotic device is operable under battery power comprising one or more batteries, which can be disposed within the device or externally to the device.

In a more general aspect, the invention is directed to an orthotic device for a joint including a frame removably fixable to a limb of a user, the frame comprising a hinge assembly disposable at a joint of the limb; a motive device mounted to the frame at the hinge assembly and operative to generate an output force or torque or to resist an input force or torque; and a gear assembly attached to the shaft of the motive device to couple an input or output force or torque to the hinge assembly. The motive device can include an electro-rheological fluid brake device and/or an electro-rheological fluid actuator. In a particular embodiment, the motive device is a brake or actuator device selected from the group consisting of DC motors, magneto-rheological fluid devices, frictional devices, electropneumatic devices, electromagnetic devices, hysteresis devices, eddy-current devices, pneumatic devices, hydraulic devices, voice-coil devices, electro-active polymer devices, ultrasonic motors and piezoelectric devices.

DESCRIPTION OF THE DRAWINGS

The invention will be more fully understood from the following detailed description taken in conjunction with the accompanying drawings in which.

DETAILED DESCRIPTION OF THE INVENTION

Figure 1:
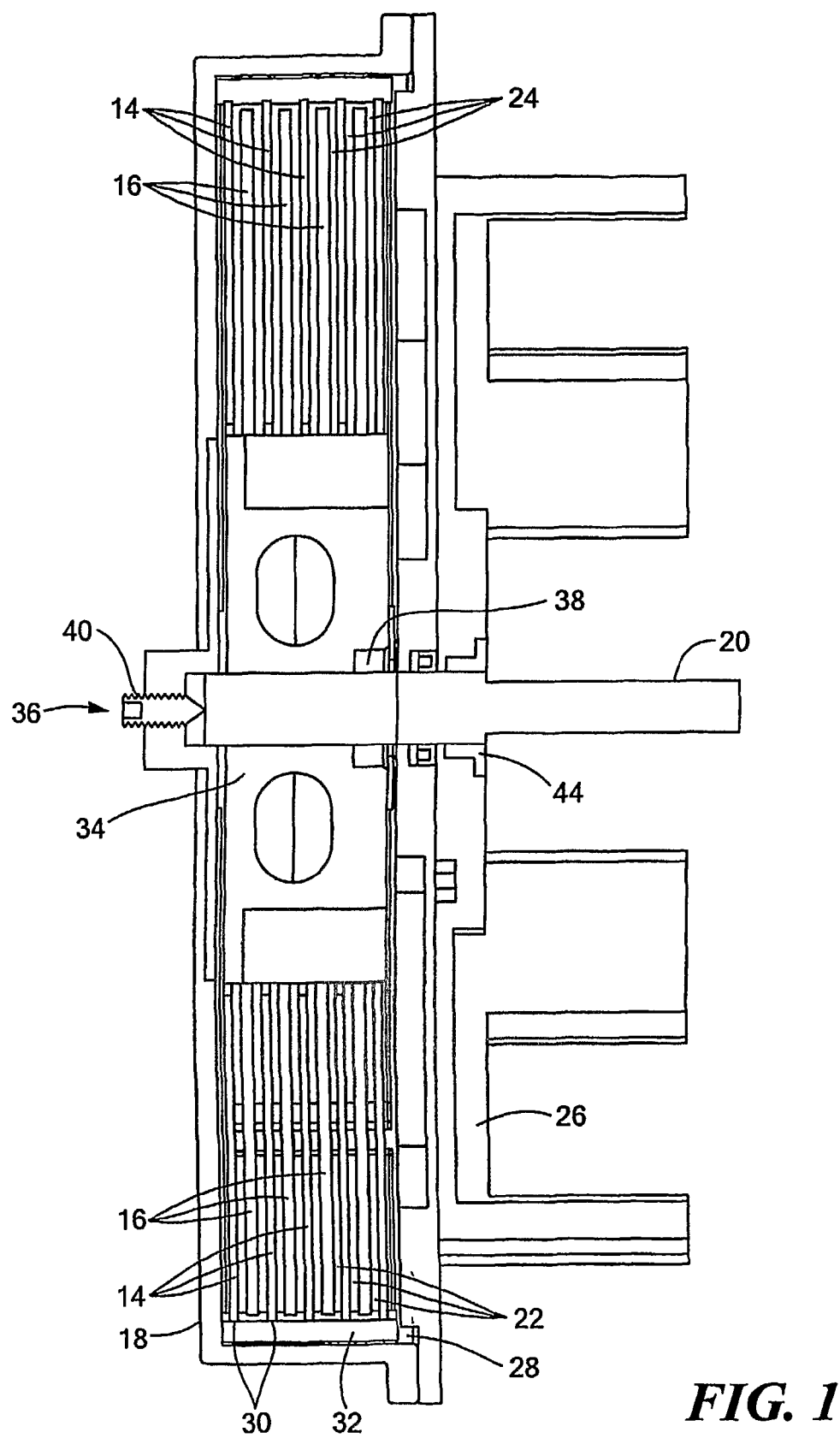
FIG. 1 is a cross-sectional view of a first embodiment of a brake or damper device of the present invention.

Electro-rheological fluids experience changes in rheological properties, such as viscosity, in the presence of an electric field. The fluids are made from suspensions of particles on the order of 0.01 to 0.1 μm in size in an insulating base fluid, such as an oil. The volume fraction of the particles is generally between 20% and 60%. The electro-rheological effect, sometimes called the Winslow effect, is thought to arise from the difference in the dielectric constants of the fluid and particles in the electro-rheological fluid (ERF). In the presence of an electric field, the particles, due to an induced dipole moment, form chains along the field lines. The induced structure changes the ERF's viscosity, yield stress, and other properties, allowing the ERF to change consistency from that of a liquid to something that is viscoelastic, such as a gel, at response times on the order of milliseconds. ERFs can apply very high electrically controlled resistive forces while their size (weight and geometric parameters) can be very small. ERFs are not abrasive, toxic, or polluting, thus meeting health and safety requirements.

Under the influence of an electric field, the state of an ERF is altered from a Newtonian fluid to a non-Newtonian Bingham plastic. As a Bingham plastic, the ERF exhibits a linear relationship between stress and strain rate like a Newtonian fluid, only after a minimum required yield stress is exceeded. Before that point, it behaves as a solid. At stresses higher than this minimum yield stress, the fluid flows, and the shear stress continues to increase proportionally with the shear strain rate.

$$\tau = \tau_y + \mu \dot{\gamma} \quad (1)$$

where $\tau$ is the shear stress, $\tau_y$ is the yield stress, $\mu$ is the dynamic viscosity and $\gamma$ is the shear strain. The dot over the shear strain indicates its time derivative, the shear rate. This is called the Bingham model.

At sufficiently high fields, the dynamic viscosity of the fluid becomes negative. This phenomenon can be explained by assuming that fewer, or weaker, bonds are formed at higher shear rates, thus giving a smaller total yield stress and the effect of negative dynamic viscosity.

The yield stress $\tau_y$ and the dynamic viscosity $\mu$ are two important parameters that affect the design of the present ERF-based brake or actuator device or orthotic device. The dynamic viscosity $\mu$ is generally determined by the base fluid with some electric field dependency, which is often neglected when using the Bingham Model. The field-induced yield stress $\tau_y$ generally depends on the electric field strength and is considered to be independent of the shear rate. For this dependence, some theoretical models have been derived, but none is yet able to reflect these relations exactly. As a rule of thumb, the yield stress can be assumed to increase quadratically with the electric field strength.

There are two important values for the yield stress: the static yield stress $\tau_{y,s}$ and the dynamic yield stress $\tau_{y,d}$. The static yield stress is defined as the value of stress needed to initiate flow, i.e., the stress needed to change from solid to liquid. The dynamic yield stress is the value of stress needed in zero-strain rate conditions to go from a liquid to solid. Which one is larger differs from fluid to fluid. Most of the time, the static yield stress is higher than the dynamic yield stress. This phenomenon, called "stiction," is highly dependent on the particle size and shape.

Another important parameter that needs to be known for ERFs is the current density J, defined as the current per unit electrode area. This parameter is needed to estimate the power consumption of ERF-based devices. Measurement of electric current through ERF materials is believed to be the result of charge leakage between particles.

ERF properties change with temperature, which can have a significant effect on the performance of ERF-based devices. Preferably, the ERF should show constant properties over a large range of temperatures. There is no unified model describing the temperature dependence of the parameters of ERFs. This temperature dependence varies from fluid to fluid. The greatest temperature problem for ERFs results from the large increase of current density with increasing temperatures. This increases power consumption but also increases safety concerns for human operators of ERF devices.

One ERF suitable for the present invention is LID 3354S, manufactured by Smart Technology Ltd. This ERF is made up of 35% by volume of polymer particles in silicone/fluorolube base oil. It has a density of $1.46 \times 10^3$ kg/m$^3$, a viscosity of 110 mPa·sec at 30° C., a boiling point >200° C., a flash point >150° C., and a freezing point <−20° C. It is insoluble in water.

In a first aspect of the present invention, a brake or damper device is provided that makes optimal use of the characteristics of an ERF to apply a resistive torque or force. Such a device is capable of slowing or stopping motion or action. (For simplicity, the device will be referred to herein as a brake device.) One or more rotating electrodes are arranged in alternation with one or more stationary electrodes. The electrodes are separated by gaps filled with a thin layer of ERF. Applying an electric field across the gaps alters the fluid's properties. More specifically, the fluid's yield stress is increased. When the rotating electrodes are in motion, the higher yield stress corresponds to an increased shear stress on the surfaces of the electrodes. The strength of the field varies in proportion to the width of the gap between the electrodes and the voltage:

$$E = V/g \quad (2)$$

where E is the field, V is the voltage, and g is the gap width between the electrodes. As the field strengthens, the yield stress of the fluid increases and the shear stress increases. The force on the electrode surfaces (the shear force) is proportional to the shear stress:

$$F = \tau/A \quad (3)$$

where F is the force, τ is the shear stress, and A is the area of the electrode surface. This force can be used for resistive control, either linearly or rotationally, depending on the configuration of the device. Using the Bingham model discussed above and electrode plates of radius r, Equations 1 and 5 can be combined and multiplied by the electrode radius r to give the resistive torque due to the ERF:

$$T=(\tau_y+\mu\dot{\gamma})Ar \qquad (4)$$

Referring more particularly to the embodiment illustrated in FIGS. 1-4, two sets of conductive electrode plates 14, 16 are oriented in alternation, with one set 14 rigidly attached to a housing or case 18 to prevent any movement, while the other set 16 is attached to a rotating input shaft 20. These alternating plates serve as the positive and negative electrodes that generate the electric field to actuate the ERF that fills the gaps 22 between the plates. The electrode assembly is placed within the insulative housing or case, filled with ERF 24, closed with a lid assembly 26, and sealed to prevent leakage of the ERF, for example, via TEFLON® seals 28.

The fixed electrode plates 14 are rigidly attached (grounded) to the case of the device. They are constructed of a lightweight conductive material such as aluminum. Small tabs 30 spaced around their edges mate to inserts 32 that slide into the case, holding the plates securely in place within the case. (See also FIG. 3.) The rotating electrode plates 16 are mounted to a rotating central mount 34. The edges of both sets of plates are rounded to minimize the "lightning rod effect," which causes arcing.

The central rotating mount 34, constructed of any suitable non-conducting lightweight material such as a composite plastic, supports the rotating electrode plates. The central mount can be hollow to reduce the weight of the device. The input shaft 20 is also attached to the central rotating mount. The rotating mount also provides a platform for adjusting plate alignment via an alignment mechanism 36.

The alignment mechanism 36 allows adjustment of the distance between the electrode plates, because the gap size is critical to proper operation of the device. For example, a set screw 40 at one end of the input shaft 20 balances the force applied by a spring 38 to the top of the rotating mount 34. Adjusting the set screw shifts the rotating mount and rotating electrodes, centering them properly between the fixed electrodes. The externally adjustable alignment mechanism reduces the need for shimming during assembly, which is a time-intensive process and requires disassembly for adjustment. The external alignment mechanism allows for quick and accurate alignment of electrodes after assembly in the case and also allows adjustment after the unit is filled with fluid.

Figure 2:
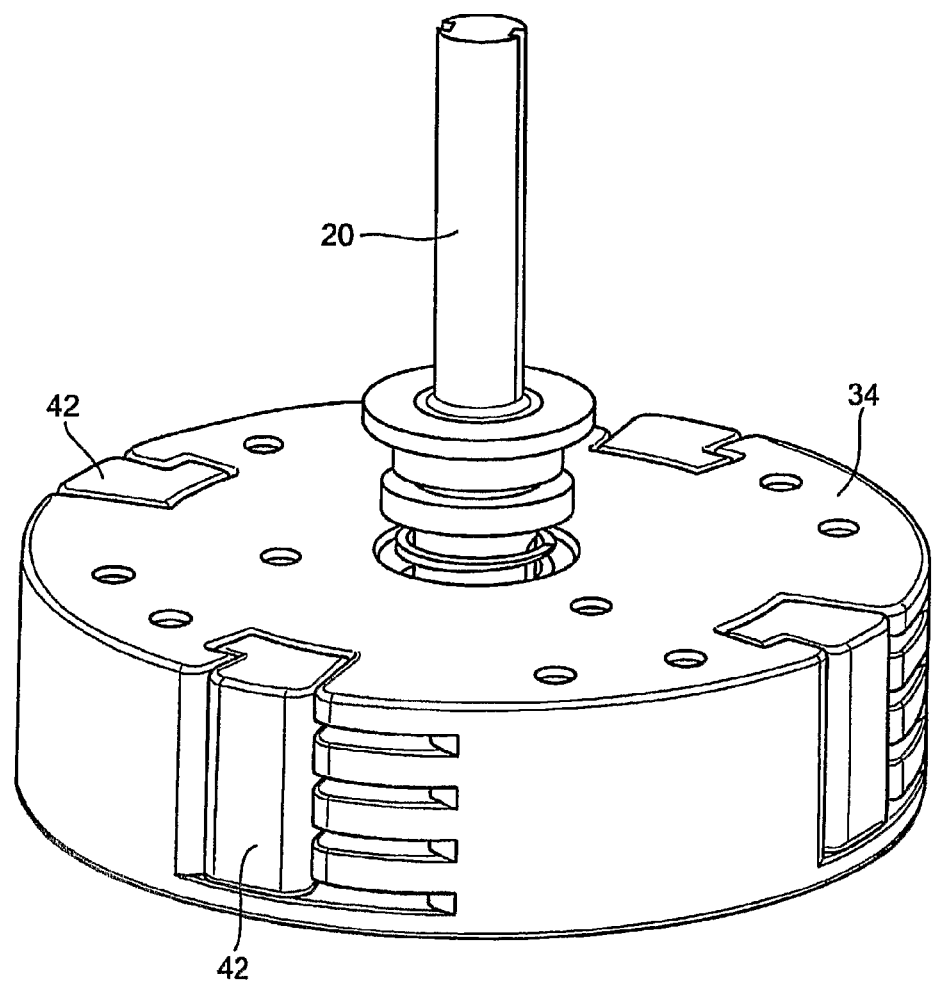
FIG. 2 is a partial view of the brake or damper device of FIG. 1.
Figure 3:
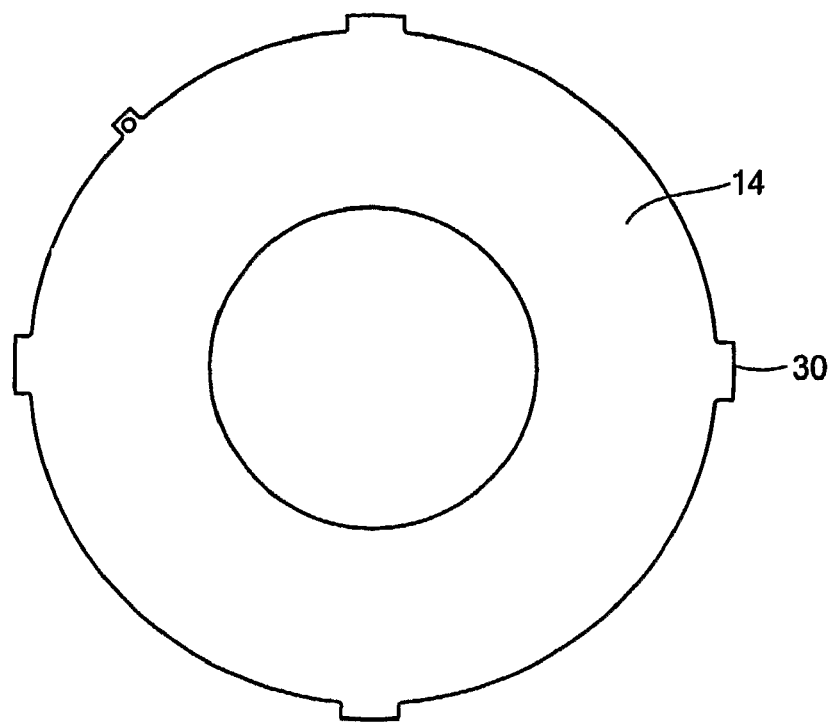
FIG. 3 is a plan view of a stationary electrode of FIG. 1.
Figure 4:
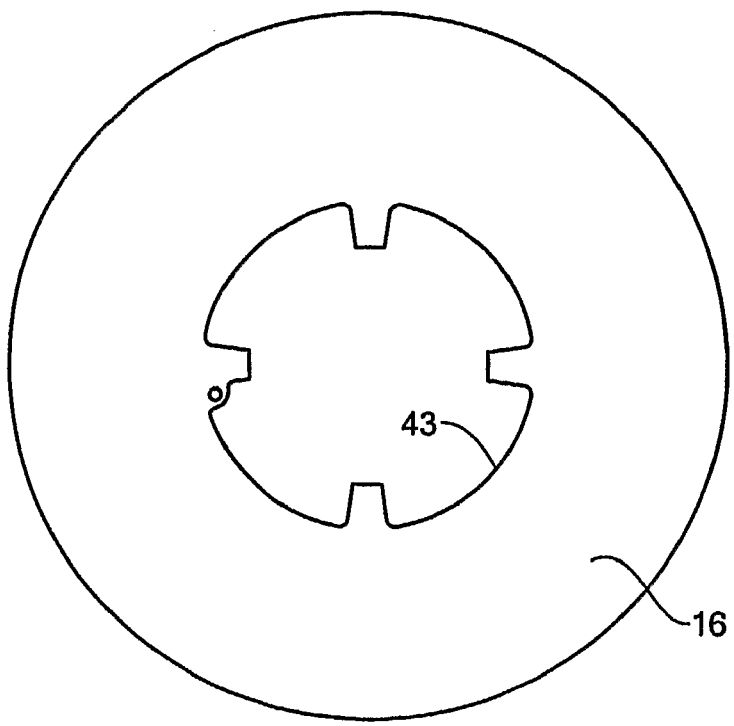
FIG. 4 is a plan view of a rotating electrode of FIG. 1.

The moving electrodes 16 mount into the central rotating mount 34 with a slot-lock system in which plate locks 42 fit within keyed slots 43 on the electrodes, as best seen in FIGS. 2 and 4. This mounting method locks the electrode plates into place and provides a rigid coupling across the plate installation slot so the rotating mount maintains strength and rigidity when torque is applied. In assembly, the moving electrodes can be mounted to the mount 34 and interleaved with the fixed electrodes that are mated to inserts 32. These components can be readily inserted as a unit into the case.

To bring power to the rotating electrodes, a rotating contact is provided. In the embodiment shown, a brush-commutator or bushing-commutator mechanism is provided. A commutator 44, a suitable bearing or bushing, is attached to the rotating central mount 34 with the commutator 44 biased into contact with the rotating input shaft 20. The commutator configuration uses silver conductive grease to stabilize resistance through the contact. Brushes carrying the actuation signal are kept in contact with the commutator via springs.

In operation, actuation of the viscous fluid 25 creates a resistive torque on the rotating input shaft 20. Maximizing the surface area that moves through the viscous fluid increases the torque or force output from the brake device, so multiple parallel rotating electrode plates are preferably used. This allows for maximum shearing surface area while maintaining a compact overall volume for the brake device.

The performance of the brake device is directly related to three factors. These are the geometry of the brake device, the input voltage sent to the electrodes, and the properties of the ERF itself. The geometry components of the actuation model are all parameters of the flat plate electrodes. These are the inner radius of the electrode plates ($r_i$), the outer radius of the electrode plates ($r_o$), the number of plates, and the gap width between plates (d). The torque output equation of the flat-plate brake device using these variables and the specific fluid properties are:

$$T = 4\pi N\left[\left(\frac{r_o^3 - r_i^3}{3}\right)\tau_y + \mu\left(\frac{r_o^4 - r_i^4}{4d}\right)\omega\right] \qquad (5)$$

where N is the number of moving plates, $\tau_y$ is the yield stress of the fluid, μ is the viscosity of the fluid, and ω is the angular velocity of the plates. Every type of ERF is composed of a different composition of suspended particles in a fluid base and thus has its own unique behavior and properties. Therefore, each ERF has its own characteristic relationship between the two and it must be known in order to derive a complete and accurate model for the brake device. After testing of the ERF LID 3354S and determining its properties (discussed above), the final modelling equation for the brake device using this fluid is:

$$T = 4\pi N\left[\left(\frac{r_o^3 - r_i^3}{3}\right)(.179E^2 + 0.253E + \tau_f) + \mu_0\left(\frac{r_o^4 - r_i^4}{4d}\right)\omega\right] \qquad (6)$$

where $\tau_f$ is the no-field frictional yield stress term characteristic to each specific brake device, $\mu_o$ is the dynamic viscosity of the fluid and is equal to 187 cP, and E is the electric field governed by the relationship:

$$E = \frac{\text{Voltage[kV]}}{d[\text{mm}]} \qquad (7)$$

The controllable ERF brake device thus operates as a braking or damping device that allows precise modulation of resistive torque while providing consistent and stable operation. The device is particularly suitable for the control of mechanical systems. It can also serve as a safety device.

The device offers several advantages over current devices. The device is internally wear free, other than the electrical contact and main seal, which are easily replaceable. The behavior of the ERF can be accurately modeled so precise control is possible. The ERF is activated using high voltage with very low current, so power consumption is very low. The electrodes serve dual functions: to harness the fluid stress and to create the field. This allows for a compact and lightweight design. The resistive strength of the device scales proportionally with the size and number of electrode plates so it is very adaptable for each application.

Figure 5:
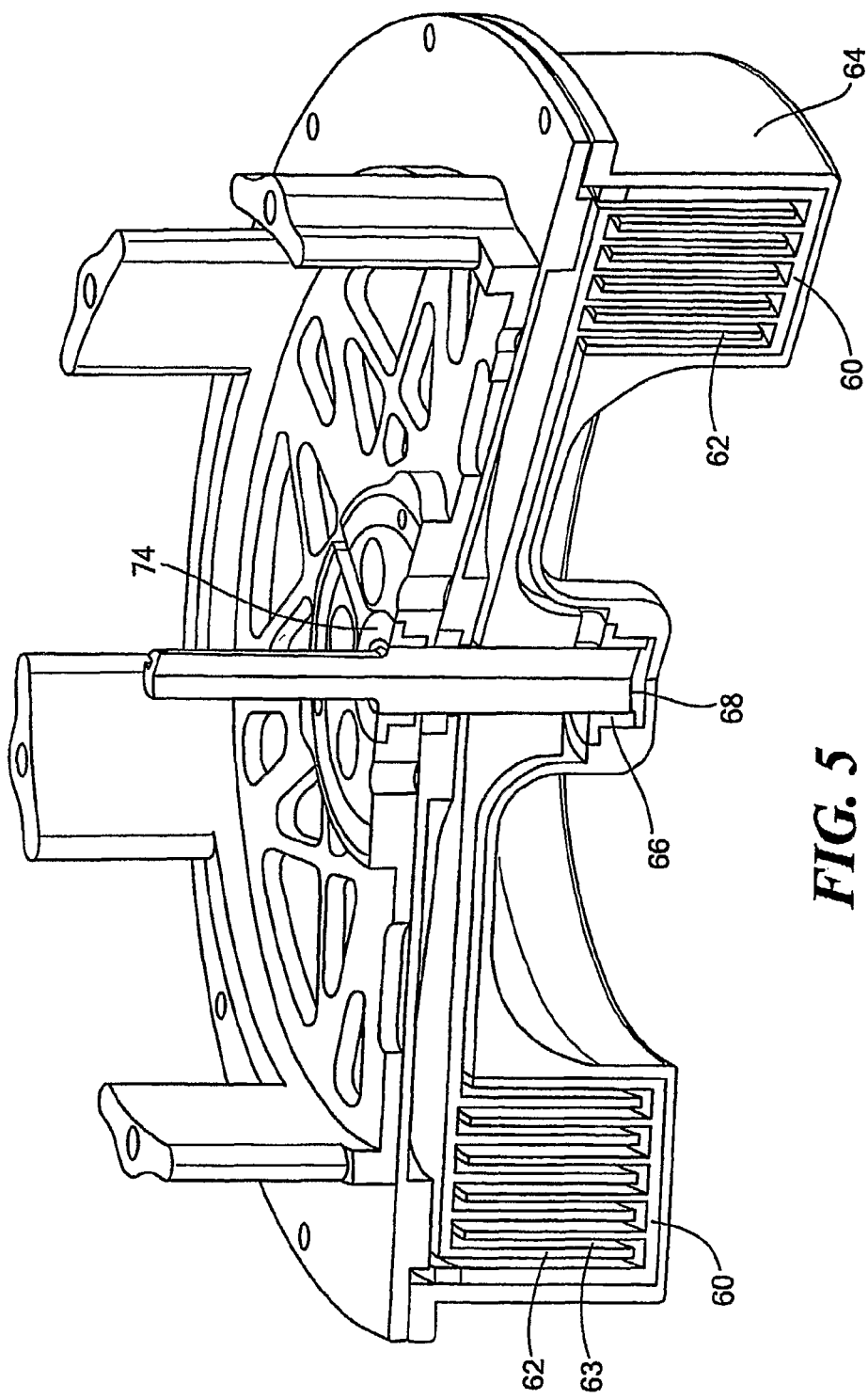
FIG. 5 is an isometric view of a further embodiment of a brake or damper device of the present invention.
Figure 6:
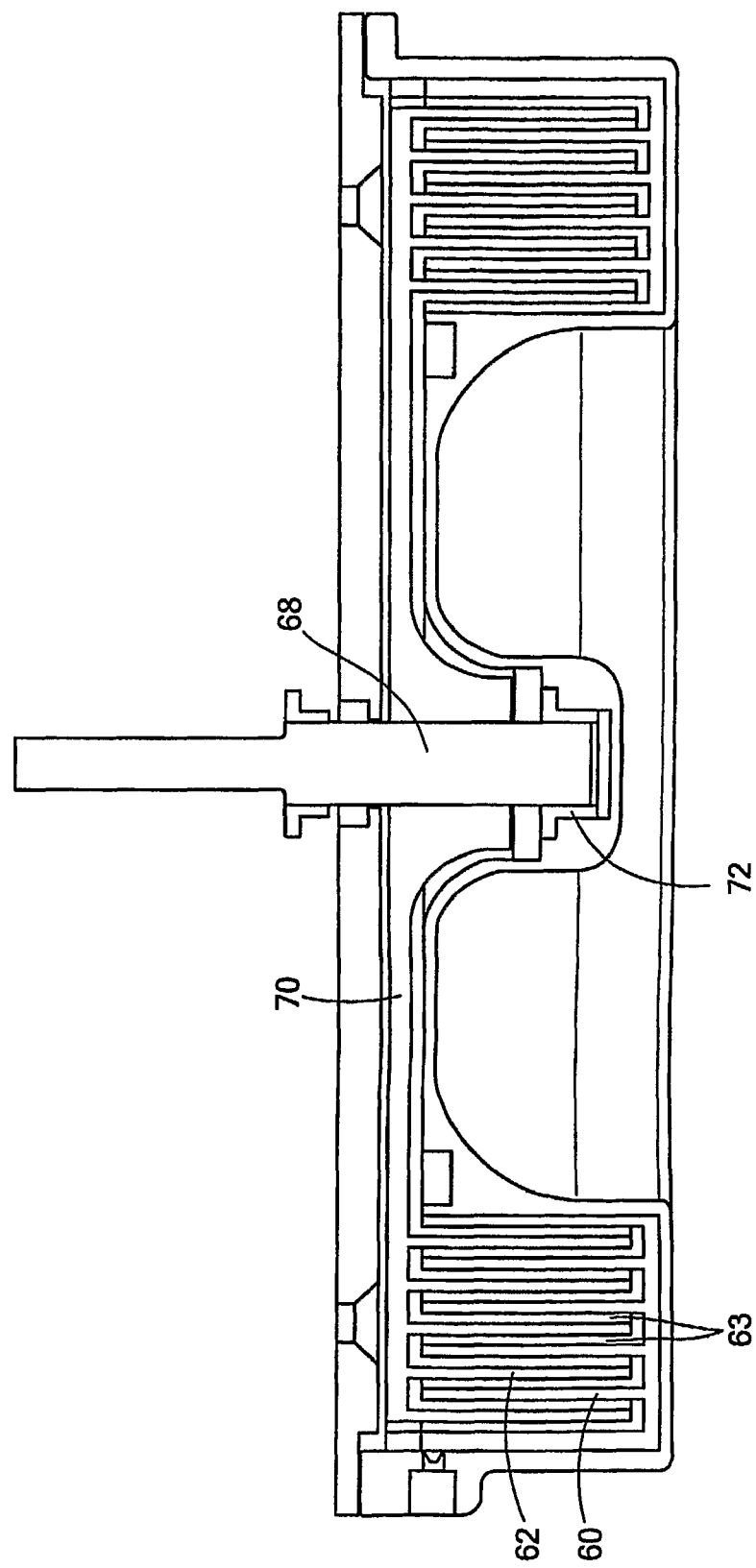
FIG. 6 is a side view of the brake or damper device of FIG. 5.

Another embodiment of an ERF brake device is illustrated in FIGS. 5 and 6. In this embodiment, one or more stationary electrodes 60 and one or more rotating electrodes 62 are configured as alternating concentric cylinders. For example, a rotating cylindrical electrode is placed concentrically between two stationary cylindrical electrodes. The cylindrical electrodes are separated only by gaps 63 filled with an ERF. Applying an electric field across the gaps alters the ERF's properties, as discussed above. To maximize the surface area that moves through the viscous fluid to increase the torque or force output, multiple concentric rotating cylindrical electrodes are preferably used. This allows for maximum shearing surface area while maintaining a compact overall volume for the resistive element.

The stationary electrodes 60 are fixed within a sealed case 64 in any suitable manner. The rotating electrodes 62 are fixed to an input shaft 68 by an extending plate portion 70. The stationary electrodes can be formed as a single integral or unitary part. Similarly, the rotating electrodes can be formed as a single integral or unitary part. Suitable bearing 72 and seal 74 are provided. An electrified bushing or bearing 66 is employed to bring power into the device.

This embodiment is advantageous in that a greater surface area of the electrodes are located radially more distant from the shaft, which increases the resisting torque.

In another aspect of the present invention, the ERF brake device is combined with an actuator, such as electromagnetic, pneumatic, or electrochemical actuators, to provide a hybrid actuator device that is capable of both resisting and applying a torque or force.

Figure 18A:
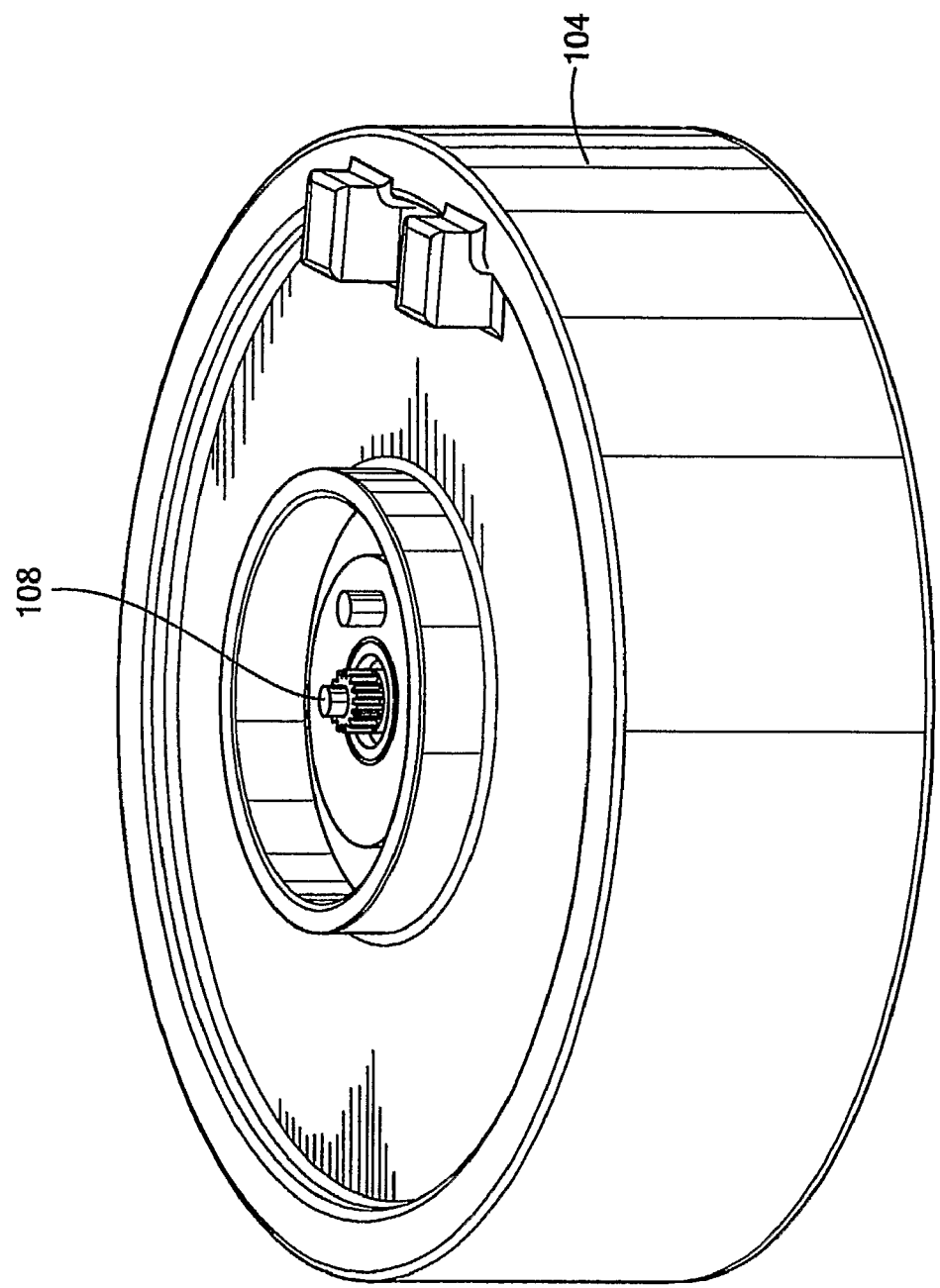
FIG. 18A is an isometric view of a case of the actuator of FIG. 7.
Figure 18B:
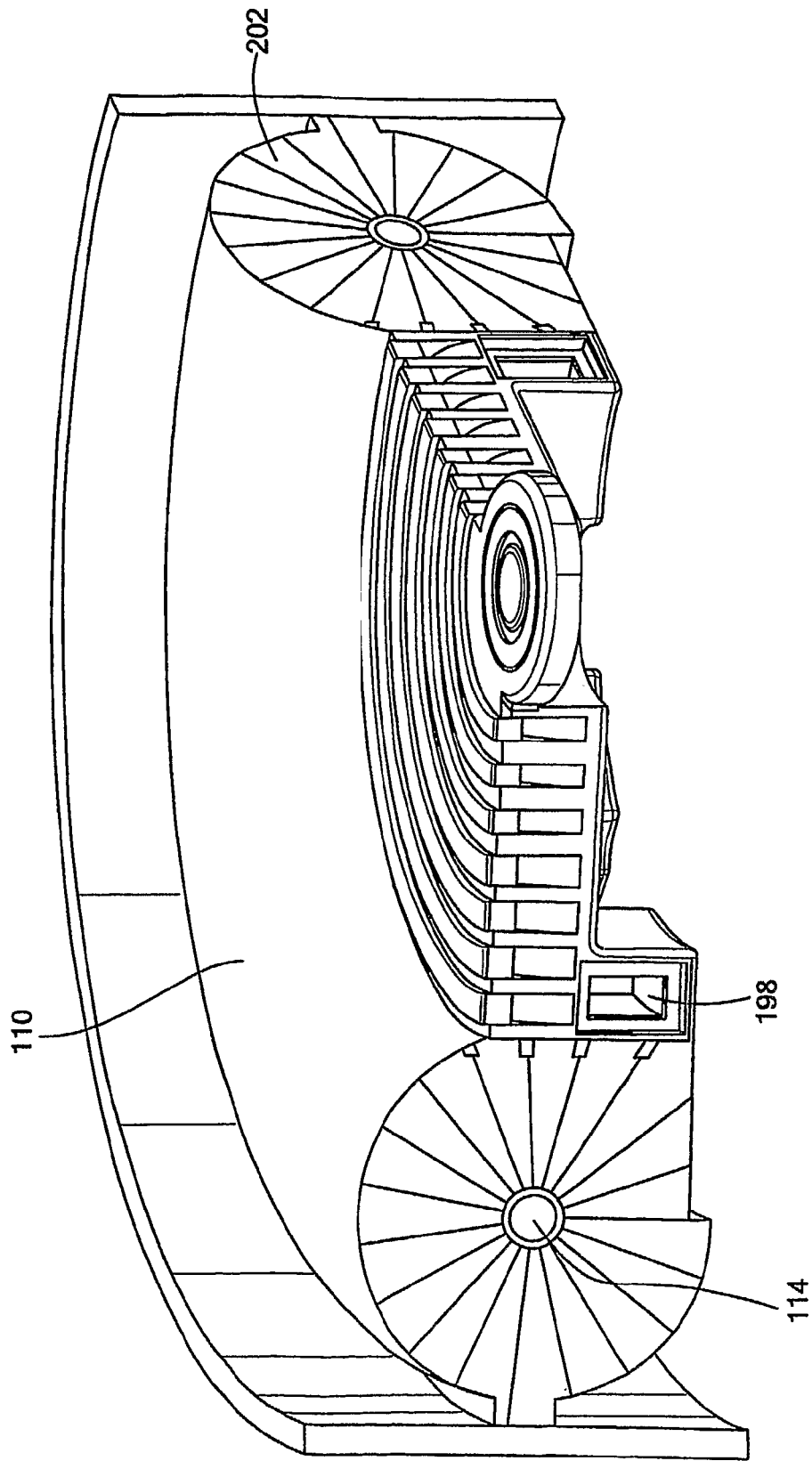
FIG. 18B is an isometric view of a stress ring of the actuator of FIG. 7.
Figure 19:
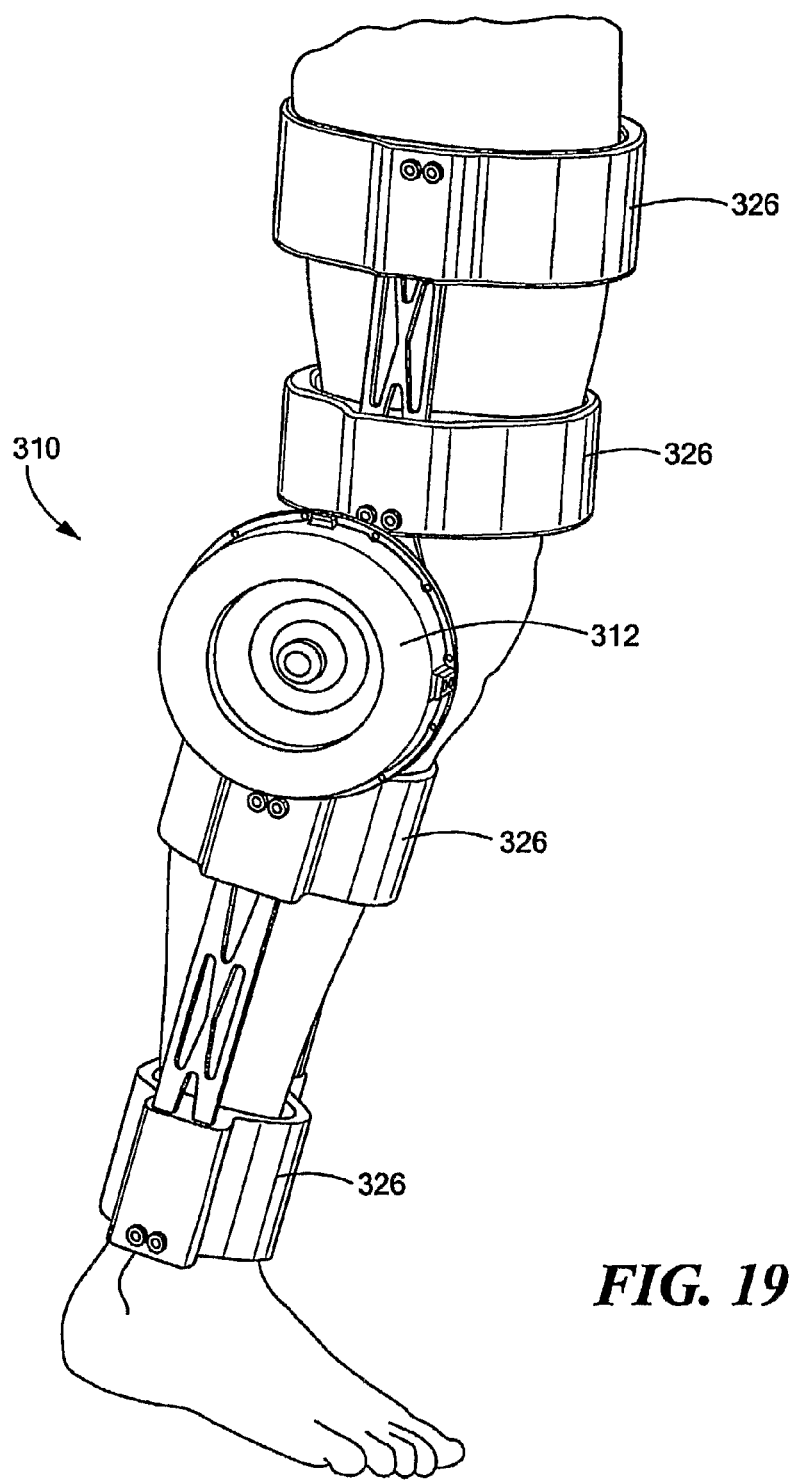
FIG. 19 is an isometric view of an orthotic device for a leg incorporating a brake or damper device and/or an actuator device of the present invention.
Figure 20:
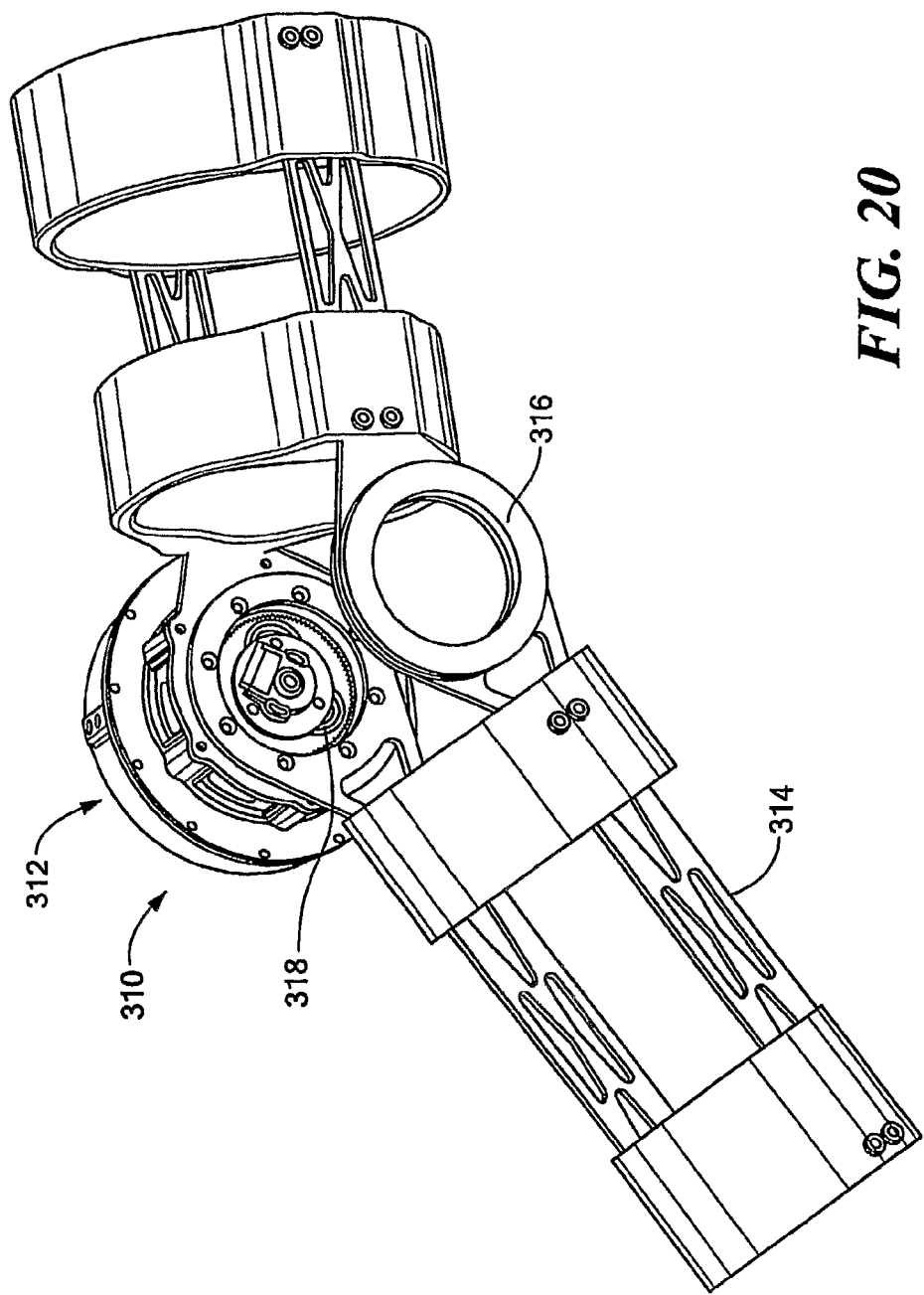
FIG. 20 is an isometric view of the orthotic device of FIG. 19.
Figure 21A:
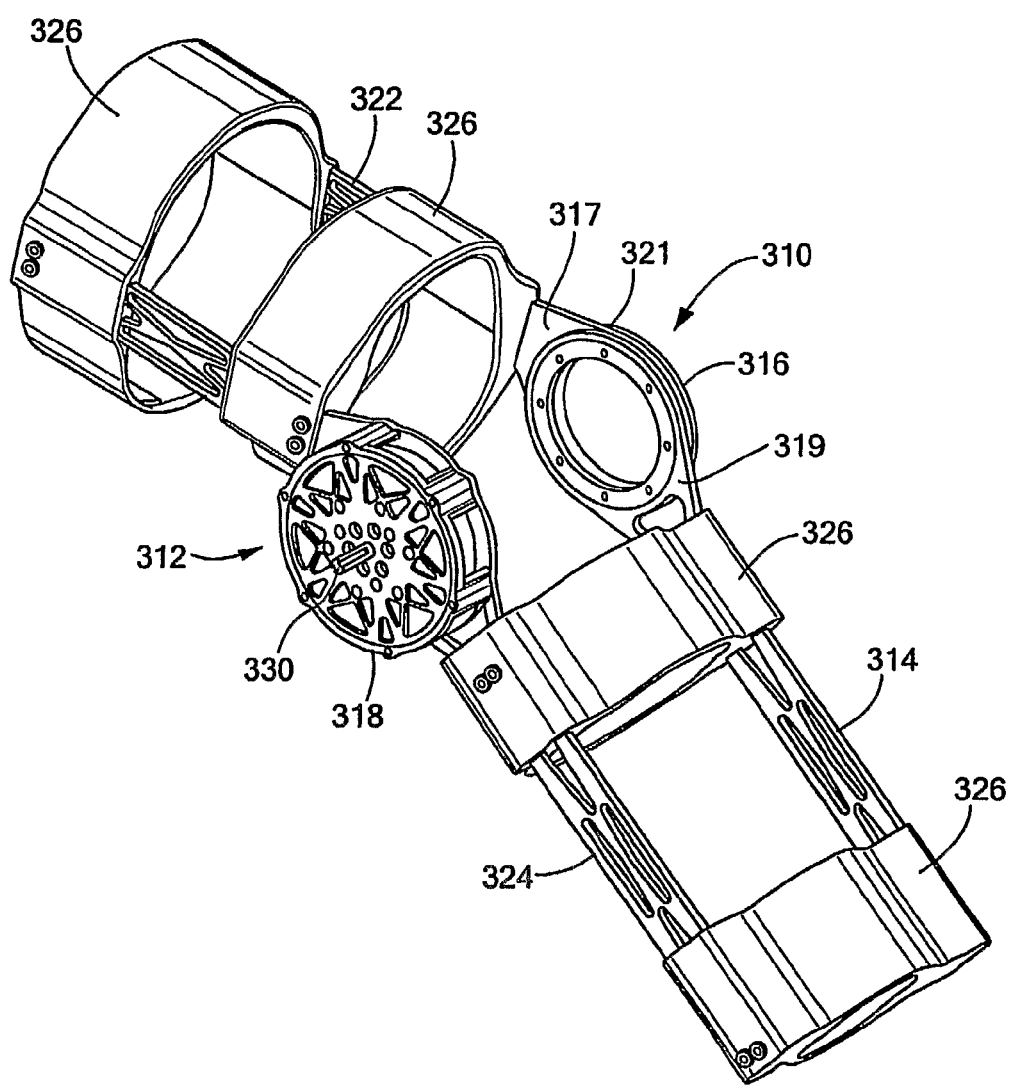
FIG. 21A is an isometric view of the orthotic device of FIG. 19 with the brake or damper device or the actuator device removed.
Figure 21B:
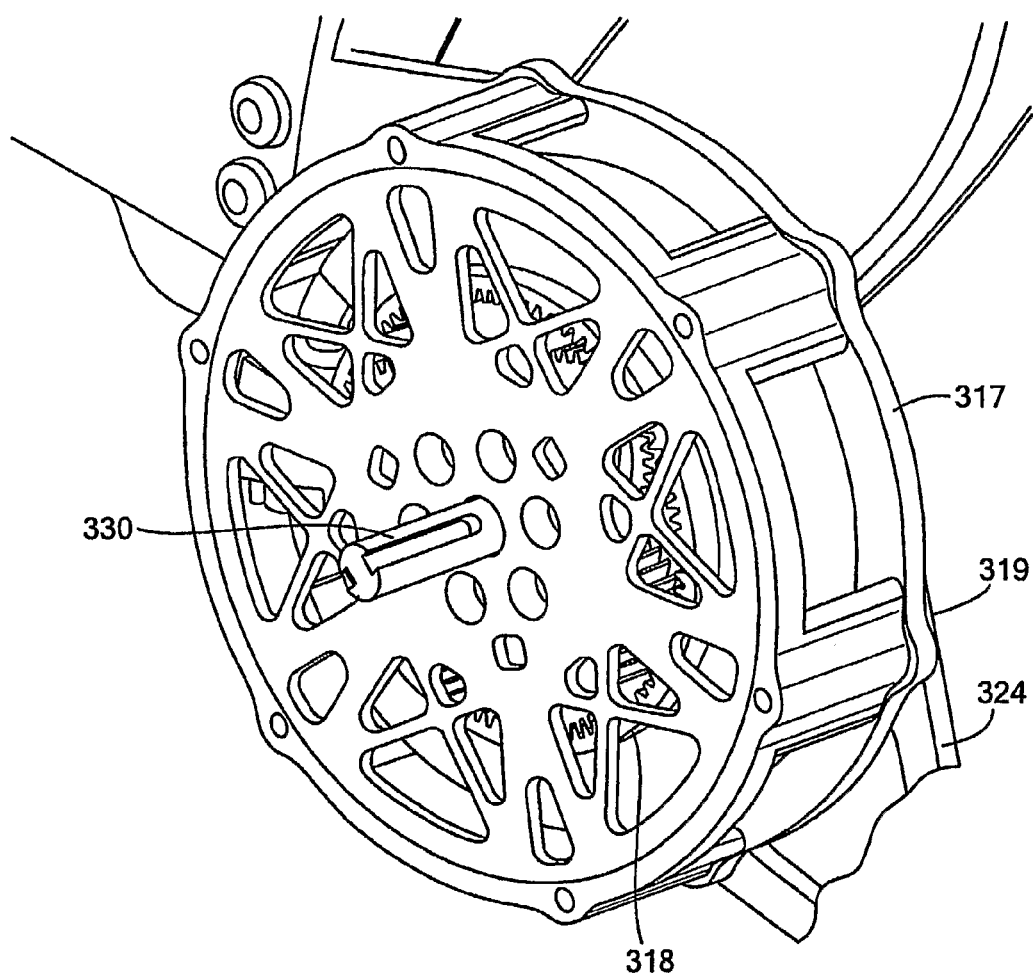
FIG. 21B is a partial isometric view of a gearbox and hinge assembly of the orthotic device of FIG. 19.

Referring to FIGS. 7-18B, fixed electrodes 102 are mounted to a housing or case 104, as shown particularly in FIG. 18A, and movable electrodes 106 are mounted for rotation with an input/output shaft 108 via rotatable members or stress rings 110. The electrodes are provided in arcuate segments of a cylinder (three in the embodiment described herein) that are independently actuatable, discussed further below. The electrodes are constructed of a lightweight conductive material. All electrode edges are preferably rounded to reduce edge effect arcing. A gap 112 between the fixed electrodes and the movable electrodes is filled with ERF. The device operates as a brake device in the manner similar to that described above in conjunction with the concentric cylindrical electrodes. The gap between the fixed and movable electrodes where the ERF is activated is critical and ranges from 1.0-1.5 mm. In the other portions of the actuator, the gap is increased to decrease unwanted forces due to zero-field fluid shear.

Figure 8:
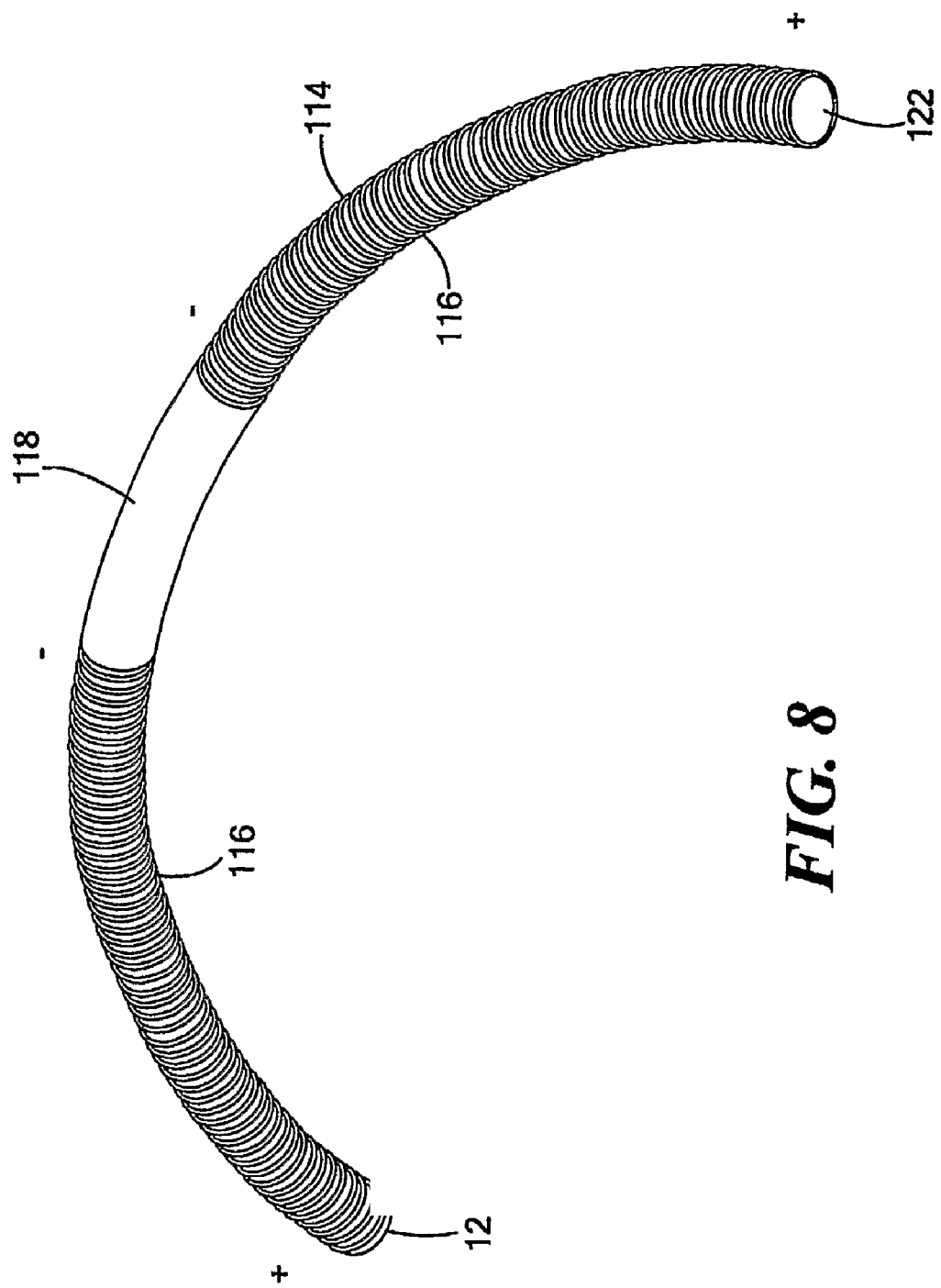
FIG. 8 is an isometric view of an electromagnet of the actuator of FIG. 7.

Additionally, a plurality of independently actuatable linear actuators is provided in arcuate segments within the device. In the embodiment illustrated, three eletromagnetic actuators 114 are provided. An electromagnetic actuator is illustrated in FIG. 8. Each electromagnetic actuator comprises two magnets 116 connected together. The core is separated in the center 118 and the windings reverse. This configuration gives each electromagnetic assembly similar poles at each end 120, 122. Each electromagnet is fixed in any suitable manner within an associated arcuate stress ring 110, to which an associated one of the movable electrodes 106 is also attached.

The case 104 houses all energized components. It is an insulator, and provides a rigid structure for the internal mechanisms to work against. Any suitable features 103 can be provided for mounting or interfacing with an application, such as a frame for an orthotic device (discussed below). A main seal 124 is a shaft seal to keep the ERF from leaking out and contaminates from entering. The fixed electrodes 102 act as common high voltage ground to all three electrodes that are mounted on the stress rings 110.

In operation, by mounting the linear actuators on the independently rotatable members, the stress rings 110, and sequentially locking and unlocking the stress rings 110 with the ERF, the linear action of the actuators is converted to discrete rotary motion. As an example, each actuation step is about 1-2 mm (0.5-2° rotationally) and they occur up to 60 times per second. The device is operative with a high power density and low energy requirements.

Figure 9:
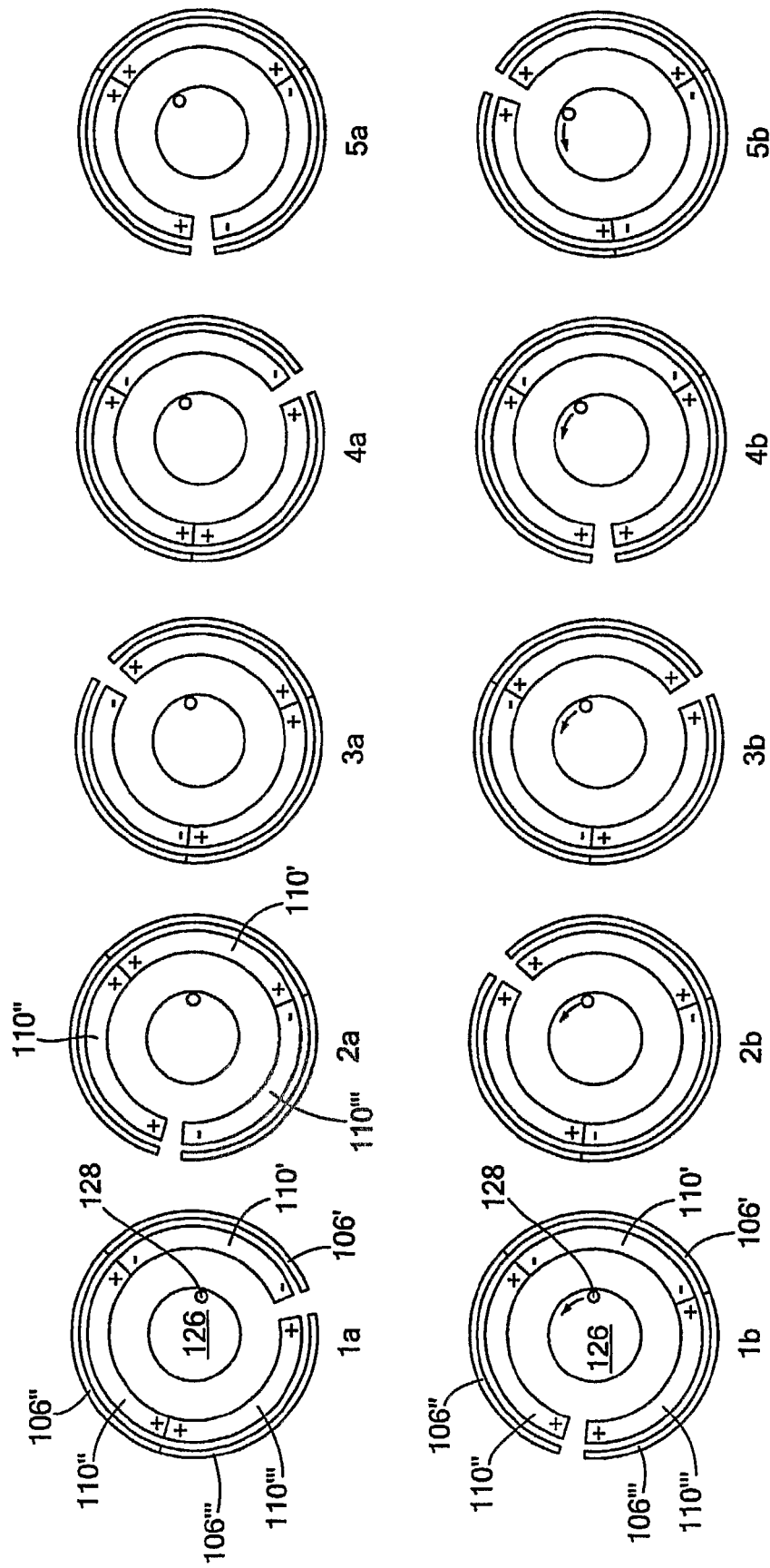
FIG. 9 illustrates schematically operation of the actuator of FIG. 7 in a torque-generating mode.
Figure 10:
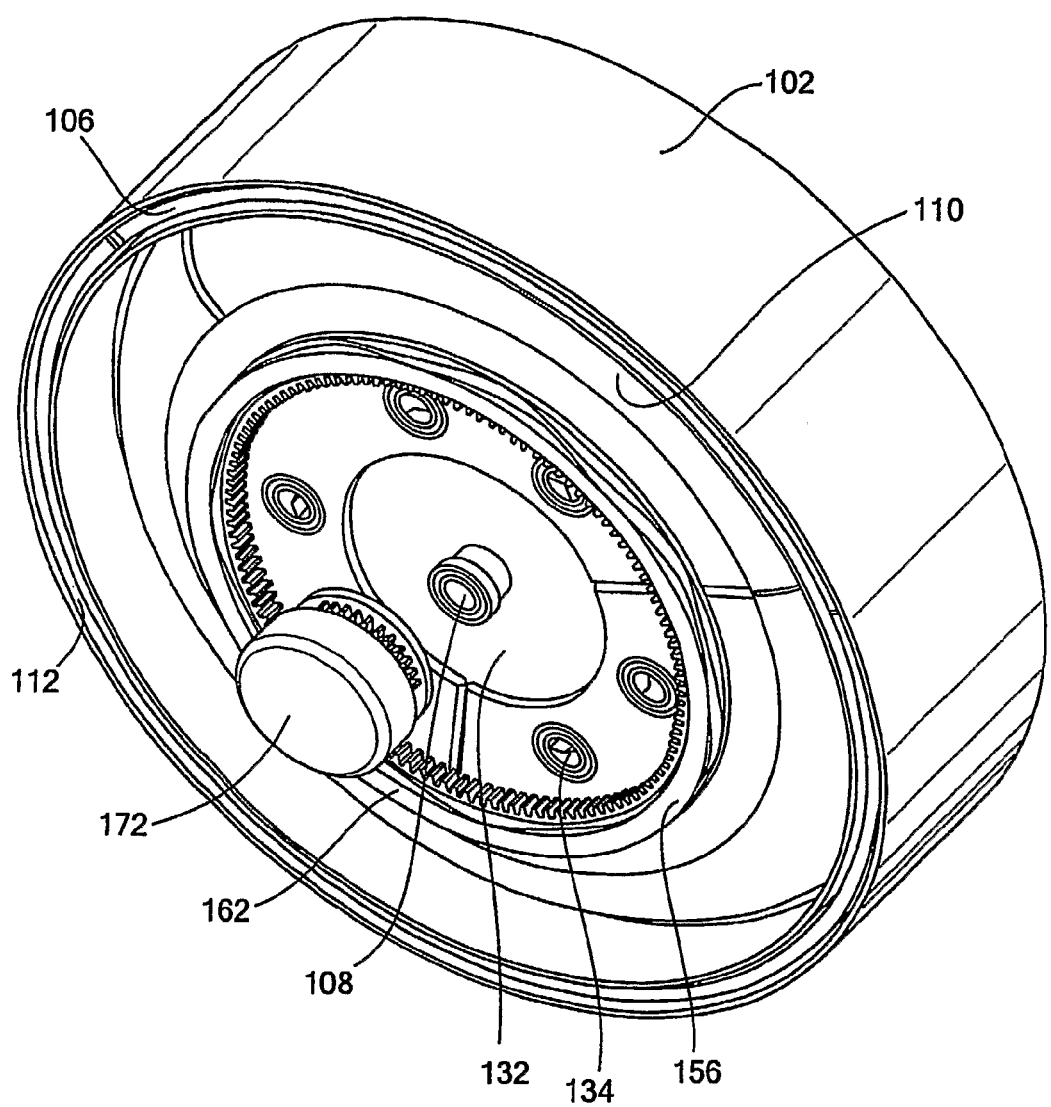
FIG. 10 is a bottom isometric view of the actuator of FIG. 7.
Figure 11:
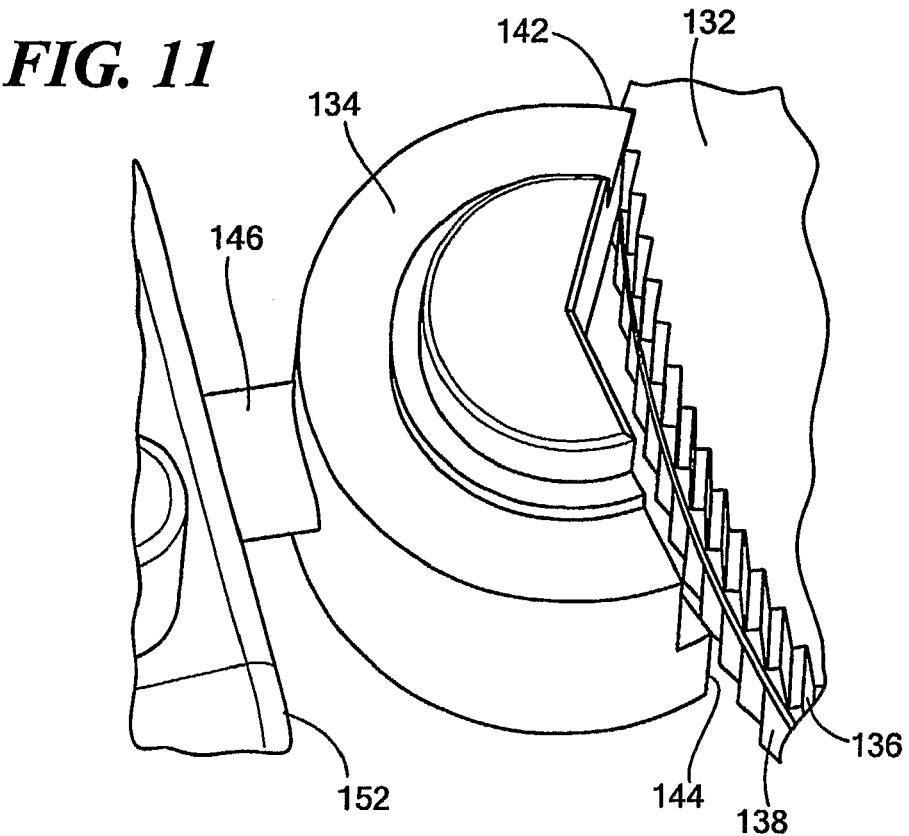
FIG. 11 is a partial view showing a ratchet cam and part of a ratchet gear of the actuator of FIG. 7.
Figure 12:
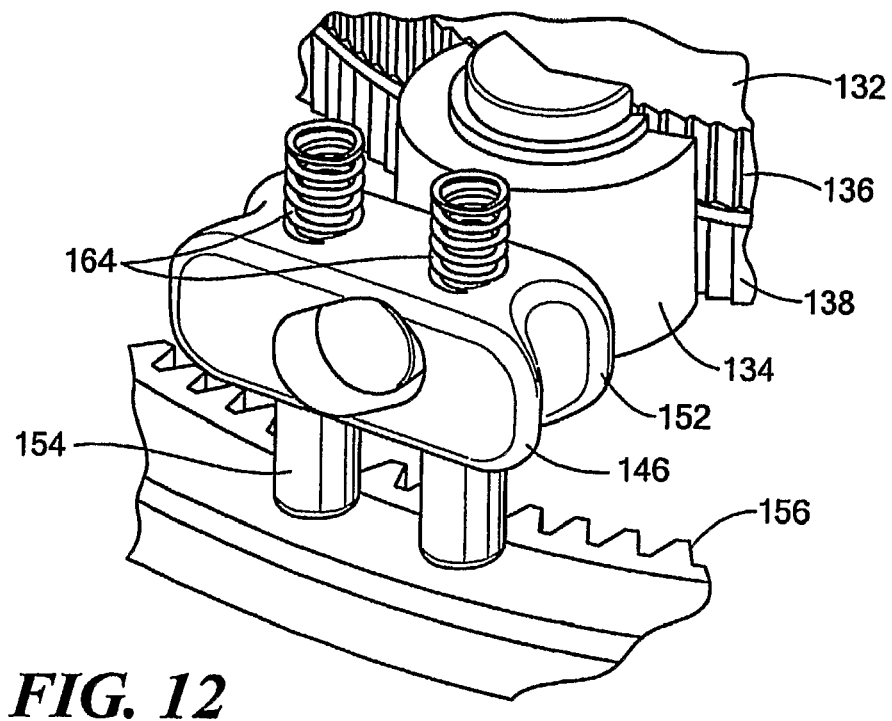
FIG. 12 is a partial view showing a directional control mechanism of the actuator of FIG. 7.
Figure 13A:
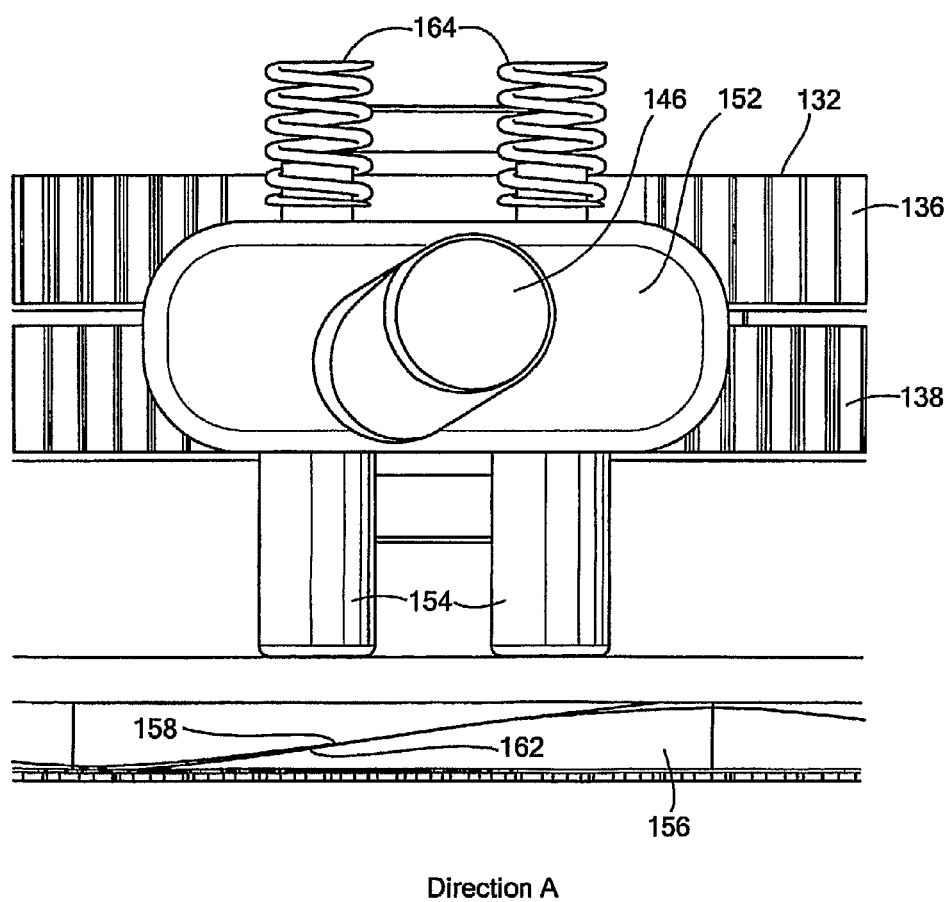
FIGS. 13A, 13B, and 13C illustrate various positions of the directional control mechanism of FIG. 12.
Figure 13B:
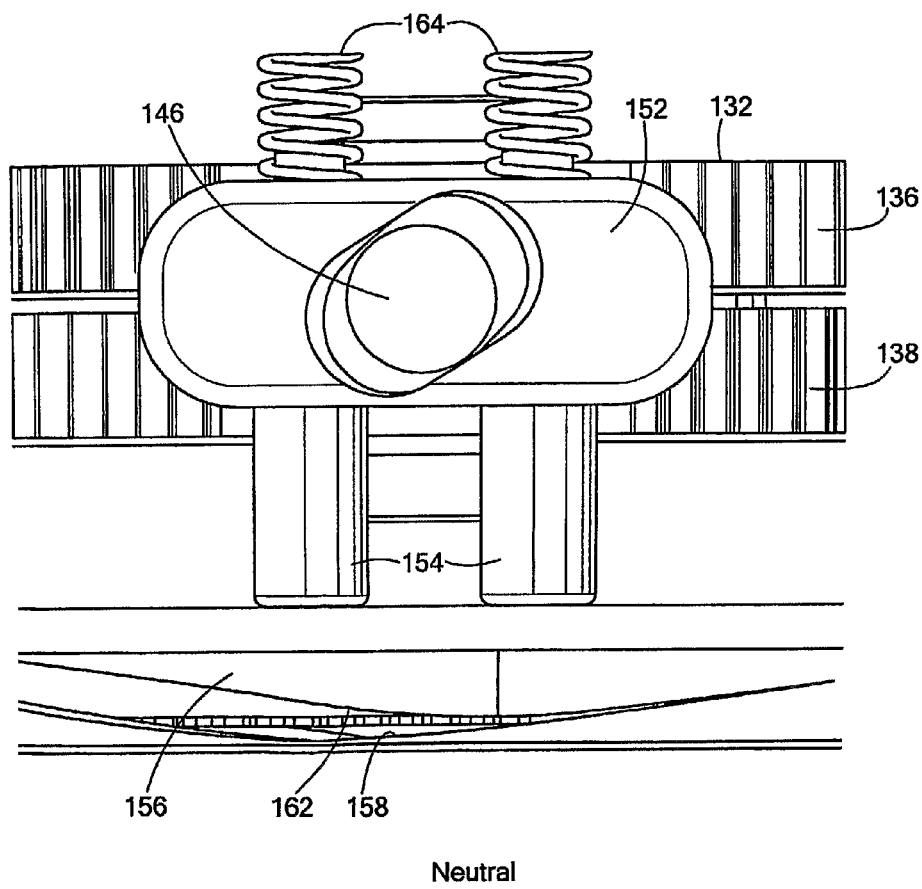
Figure 13C:
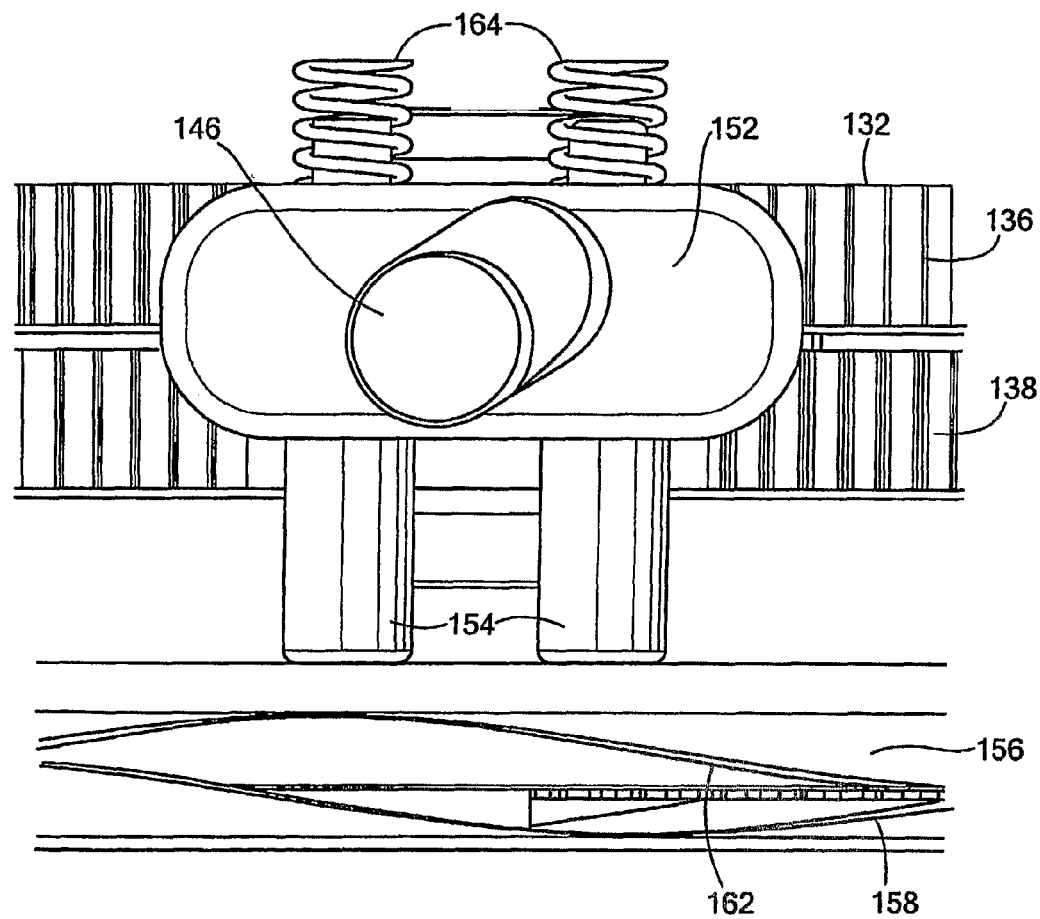
Figure 14:
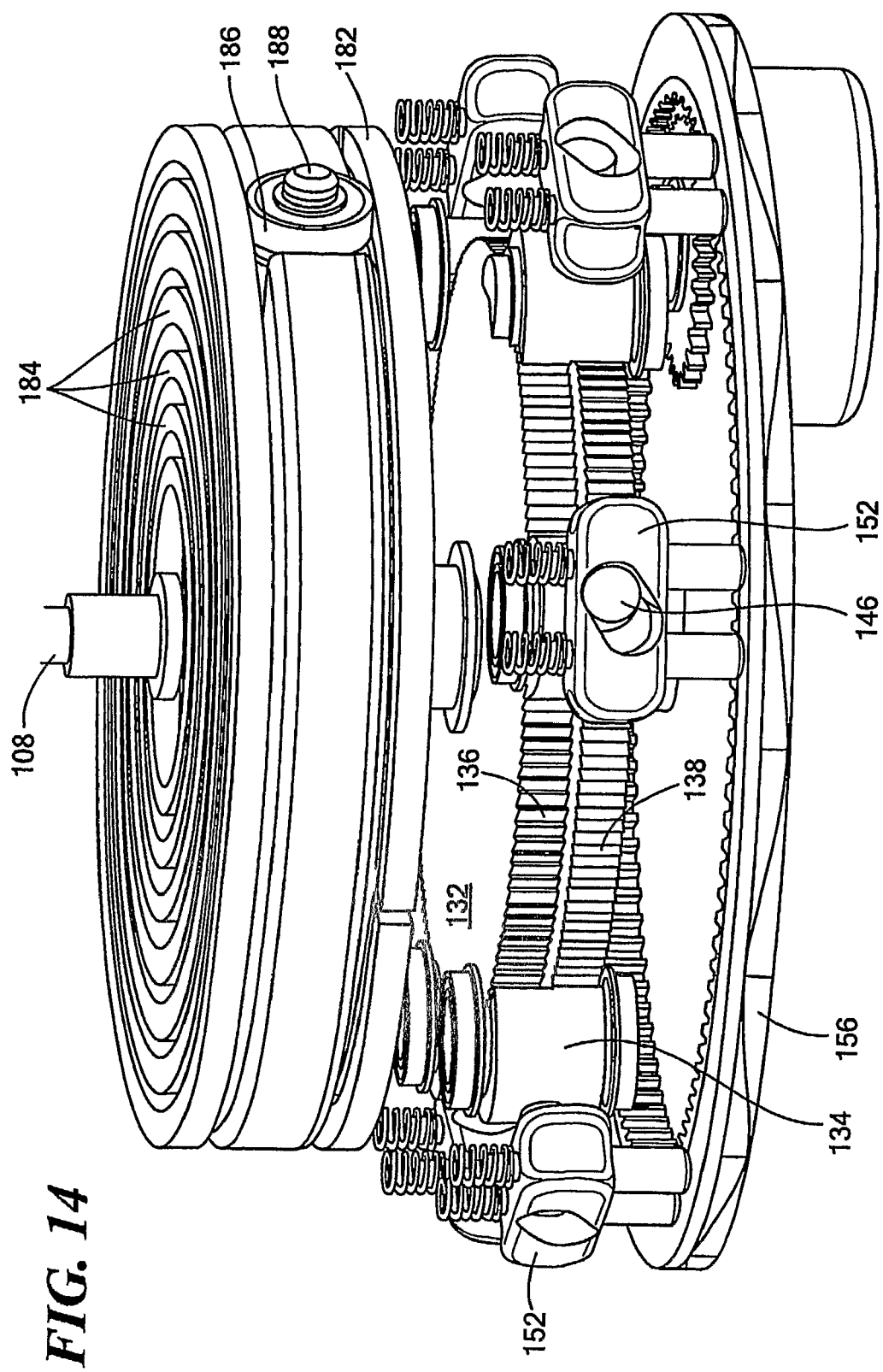
FIG. 14 is an isometric view of the actuator of FIG. 7.

A diagram detailing the internal operating sequence is shown in FIG. 9. The top row illustrates the start of a cycle, and the bottom row illustrates the end of that cycle. Each stress ring 110', 110'', 110''', encompasses an independent linear actuator, the electromagnet. The outer rings represent the ERF rotating electrodes 106', 106'', 106'''. The central circle 126 schematically represents a ratchet mechanism that connects the motion of the stress rings to the input/output shaft 108. This ratchet mechanism is described further below. The white dot 128 on the central circle schematically shows the movement of the ratchet mechanism, and consequently of the input/output shaft.

In cycle 1, at step 1a, the rings 110', 110''' are locked to the case using activated ERF. The ring 110'' is the active ring driving the shaft. The opposing polarity between electromagnets of stress rings 110' and 110''' drives the device one step, illustrated in step 1b. At step 2a, the rings 110' and 110''' are locked to the case. The polarity of electromagnet at ring 110''' is reversed, driving the electromagnet of the active ring 110'' toward the electromagnet of ring 110''', illustrated in step 2b. Motion continues in this manner.

As noted, actuation takes place sequentially on three independent stress rings. This sequential motion is transferred to the output shaft using a ratchet mechanism. This mechanism is able to ratchet in one direction during use in torque generation mode and additionally is able to lock all the stress rings in resistive mode so the input torque is distributed evenly to all three rings.

Referring to FIGS. 7 and 10-14, a ratchet gear 132 is fixed to the shaft 108. The ratchet gear has upper and lower rows 136, 138 of opposed gear teeth that allow rotation in one direction while locking rotation in the opposite direction. At least one ratchet cam 134 is associated with each stress ring. Each ratchet cam has two locking faces, an upper face 142 for locking against the upper teeth on the ratchet gear and a lower face 144 for locking against the lower teeth on the ratchet gear. The cam is pivotable between one position allowing motion in one direction and another position allowing motion in the opposite direction. The cam can also be positioned in an intermediate neutral position that allows free rotation of the shaft.

In operation to generate active torque, the ratchet cams 134 of the stress ring that is in motion lock onto the ratchet gear 132 forcing it to rotate. The other ratchet cams (on the other two stress rings that are grounded to the case using the ERF coupling) are oriented to allow this rotation without resistance. To increase the resolution of the ratchet mechanism, the two cams in each stress ring are offset by ½ gear tooth. This effectively doubles the resolution relative to the ratchet gear.

Each ratchet cam 134 is attached to an elastic rod 146 that extends through an opening defining a cam surface 148 in a cam follower component 152. As the cam follower component moves up or down, the elastic rod travels along the cam surface in a manner that causes the ratchet cam to pivot. The cam follower component is formed of a non-stick material such as TEFLON® or similar to facilitate smooth sliding action. So that the cam follower component can move up and down, a directional slider 154, shown as a pair of legs, extends from the cam follower component to contact a sinusoidal surface assembly 156 having two sinusoidal surfaces 158, 162. One surface 158 is fixed to the case. The other two degree of freedom (DOF) sinusoidal surface 162 is rotatable, lifting the slider 154 as it moves, illustrated in FIGS. 13A-C. Springs 164 offset the upward force of the directional slider. The control of the sinusoidal surface assembly is provided by a pinion 166 and internal gear 168.

The pinion can be driven automatically under computer control or manually by an external knob 172. The low torque requirements of the slider control system facilitate the use of a lightweight and compact device, such as an ultrasonic motor, servo motor, DC motor. Alternatively, a simple knob can replace the actuator if automated directional control is not needed. In this case indents can communicate the internal positioning of the directional control system.

Figure 7:
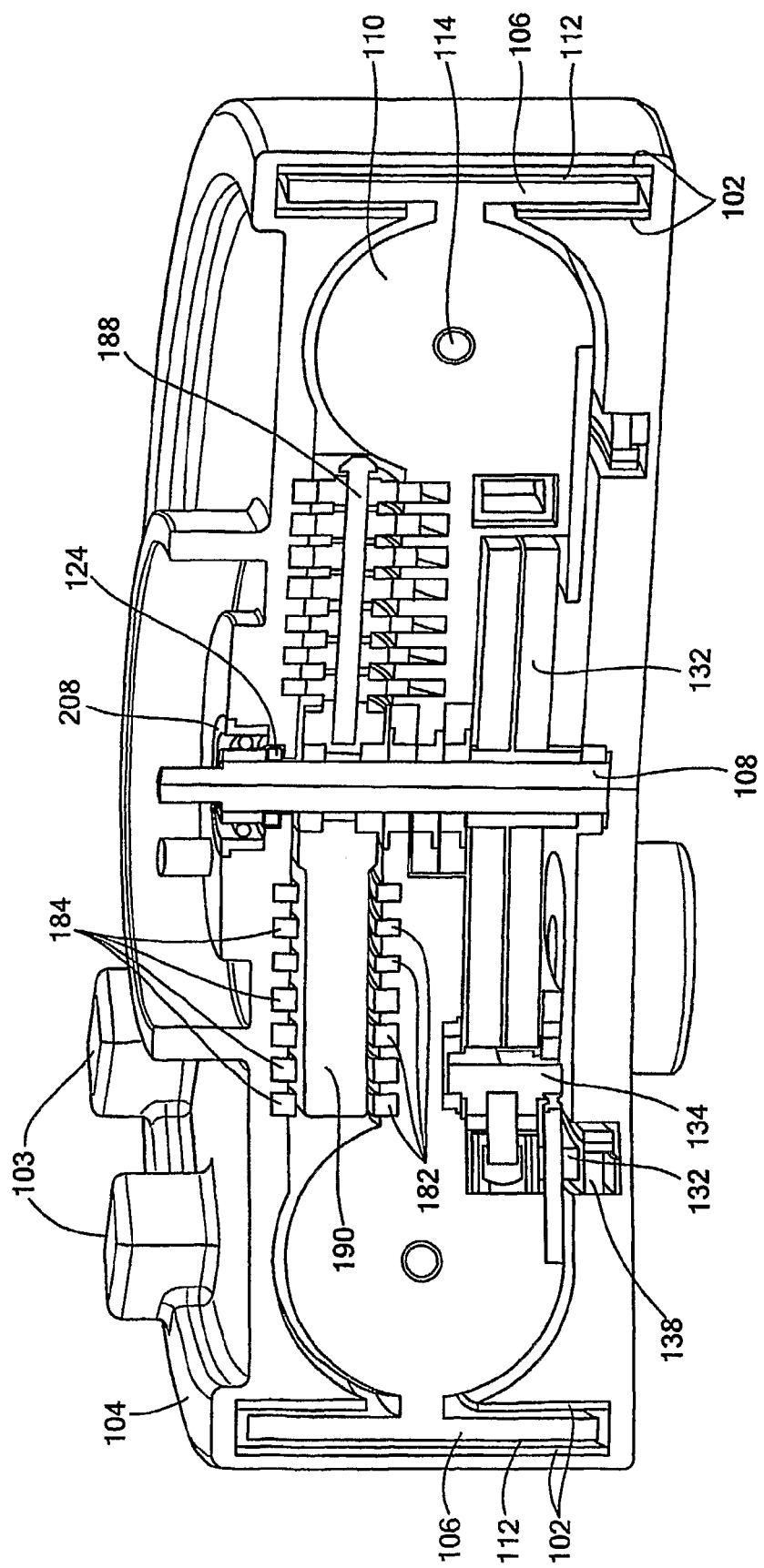
FIG. 7 is a cutaway isometric view of an embodiment of a resistive and torque generating actuator of the present invention.
Figure 15:
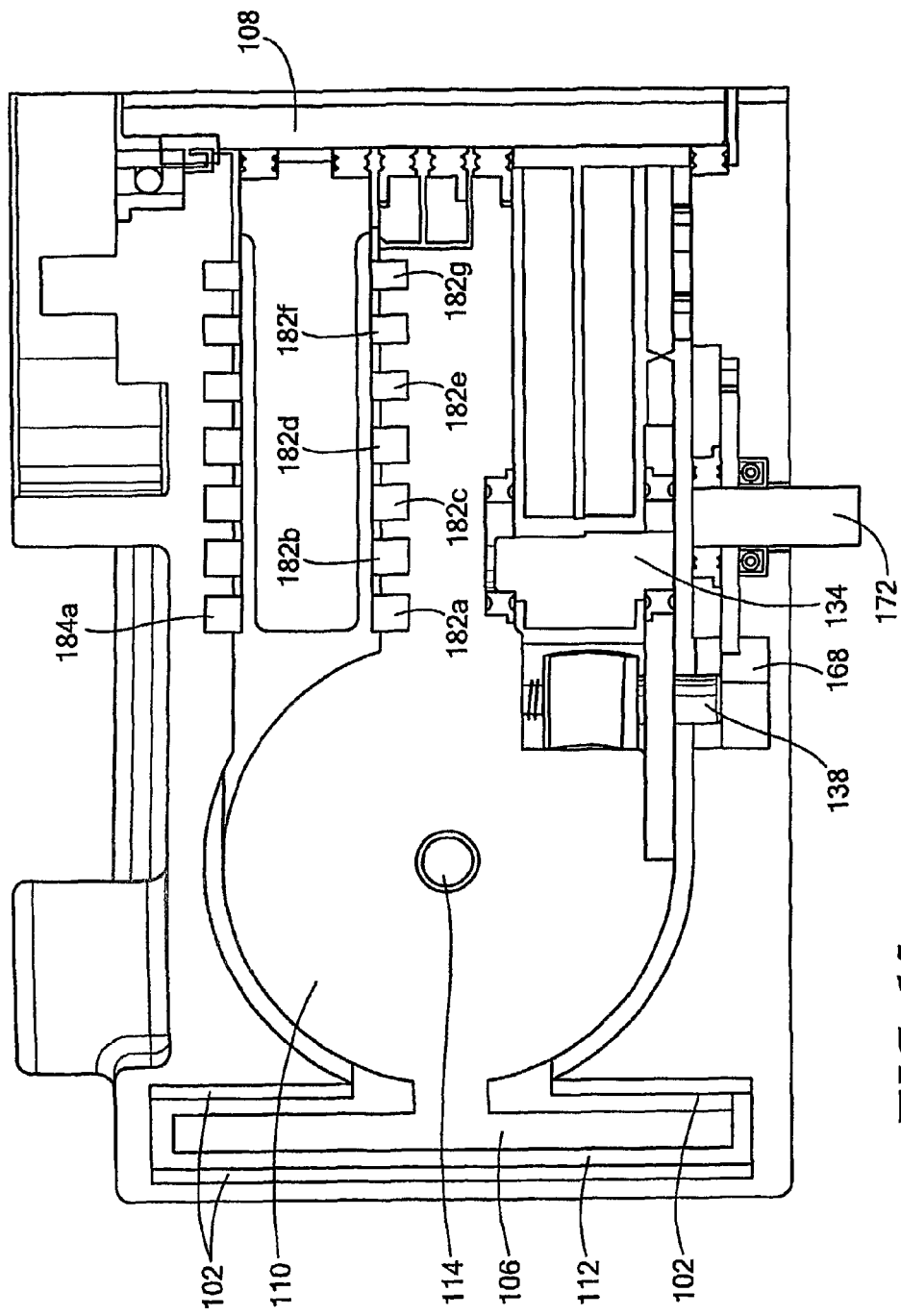
FIG. 15 is a partial sectional view of the actuator of FIG. 7.
Figure 16:
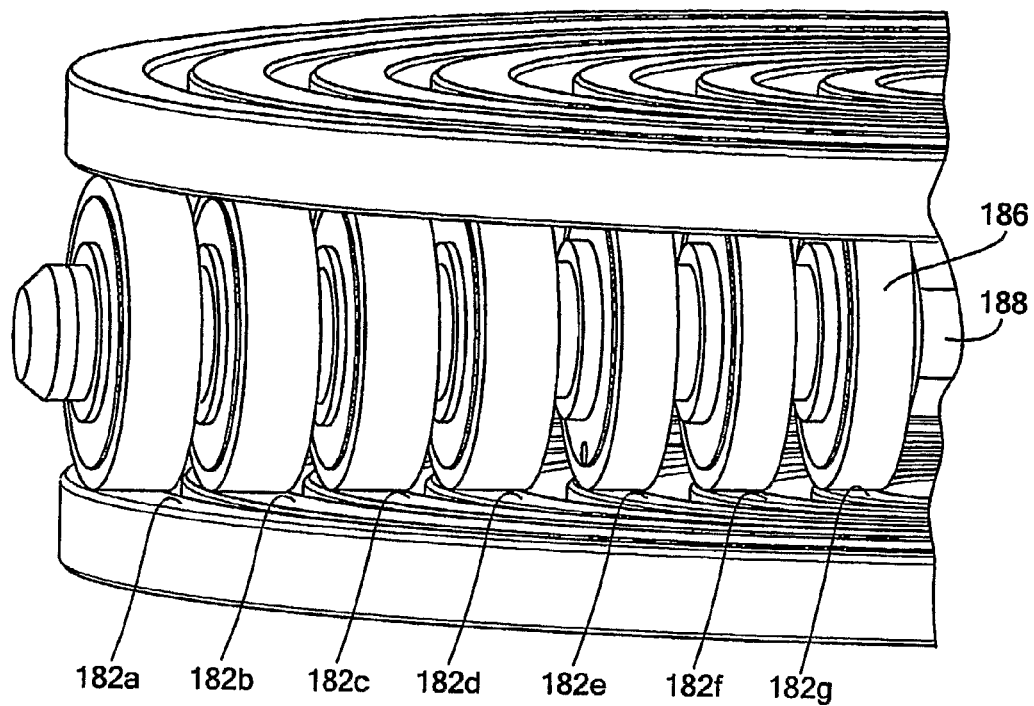
FIG. 16 is a partial view of rolling contacts of the actuator of FIG. 7.
Figure 17:
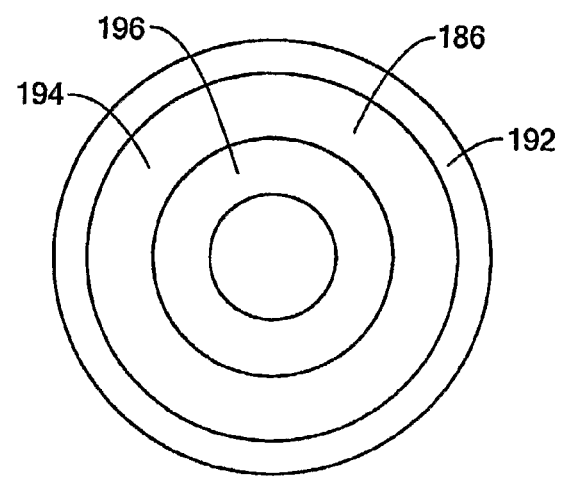
FIG. 17 illustrates a single rolling contact.

The electrical components access two independent channels for each stress ring and one ground. One channel is for high voltage control (for the electrodes 106) and one is for low voltage control (the electromagnets 114) for each stress ring, and the last is for a low voltage ground. Referring to FIGS. 7, 15, and 16, a set 182 of annular contacts is located on the stress rings to move therewith. A corresponding set 184 of annular contacts is fixed to the case. The annular contacts extend between the stress rings by a flexible spring or ribbon conductor (not shown) when there is only one set of roller contacts (discussed below). Referring to the embodiment in FIGS. 15 and 16, the contact 182a is a ground. The contacts 182b, 182c, and 182d connect to the three electromagnets in each stress ring respectively, via, for example, a wire or other conductor (not shown) through the stress ring. The contacts 182e, 182f, and 182g connect to the high voltage electrodes 106, also via, for example, a wire or other conductor through the stress ring (not shown).

A radial rolling contact system is used to transfer power from the fixed contacts to the moving contacts. A conductive roller 186 between each fixed and each moving contact is provided, which travels along each annular contact as the stress ring moves. The conductive rollers are arranged on an axle 188 extending radially outward. This system offers multiple contacts in a compact space with electrical channels extending radially from the rotating axis. For this design a single set of rollers is included, but multiple roller sets can be used to accommodate greater current requirements. Note that the thickness of each band can be adjusted up to the point when electrical noise due to slippage becomes problematic. A spacer 190 is, also provided to fill space within the case to minimize the amount of ERF needed.

The roller/rotating contacts 186 are constructed with a thin conductive outer layer 192, and then an elastic middle layer 194 and a hard bushing 196 for low friction rotation. See FIG. 17. The thin outer layer deforms to form a larger contact patch. The rotating contacts revolve around the central actuator axis while rotating around their own axis. The elastic interior also allows for easy transfer between stress rings.

This device has five modes of operation: two modes of rotational damping/braking, one for each direction, two modes of actuation, one for each direction, and a neutral/free wheeling mode where the device has only a slight effect (momentum of the ratchet only) on the input. This is important for safety and industrial use because it eliminates the need for an additional clutch to disengage the device.

As noted above, the stress rings house the linear actuators/magnets, support the electrodes, and house the ratchet system and directional sliders. They also include pressure relief chambers 198 that are filled with non-reactive elastic material, such as a compressible closed cell foam. See FIG. 18B. These chambers allow the ERF to expand due to temperature changes, absorb energy waves propagating through the fluid to dampen vibration, and help stabilize internal pressure differentials generated by quickly moving interior components. Damping channels 202 (see FIG. 18B), which dampen the vibration and shock of the ring movement, can be formed on the ends of each stress ring aligned radially. The stress rings can be configured to accommodate several types of linear actuators, including piezoelectric stacks, solenoids, EAP actuators, as well as the cored electromagnets illustrated.

Any suitable torque multiplication/reduction gearing can be coupled to the input/output shaft 108, depending on the application. Any combination of gears can be added to the actuator to balance the actuator's output, resistive torque, and velocity to each application's requirements. Standard and thin section bearings 208 are used throughout the device to ensure frictionless reliable operation.

To control vibration a damping counterweight (not shown) can be included. It is coupled to the input/output shaft and operates in the reverse direction of the stress rings' motion to offset their rotating inertia forces.

Various types of internal actuators can be employed in the present invention. In the above described embodiment, an electromagnet is provided. The electromagnet is a current controlled component that harnesses the magneto-motive force (MMF) that is generated by current flowing through multiple turns of a wire surrounding a magnetically active core. Alternatively a solenoid actuator can be employed. The solenoid is a self-contained electromagnetic linear actuator that includes an electromagnet and a movable soft iron core (the plunger). The present fluid actuator can use the force and displacement of the plunger. In a further alternative, a piezoelectric actuator employs a piezoelectric material that deforms in response to the application of voltage. Using many layers of material in series leads to a usable amount of strain. In another alternative, electro-active polymers (EAP) are materials that change shape under an electric field. They can be configured in sheet or tape form.

As an actuator, the device is easy to control, is compact, and is lightweight. The efficiency of the device is high and its overall power consumption is good. It also scales well in a predictable manner. As a resistive control device, damper, or brake, the device operates with low power consumption. It exhibits essentially no wear with respect to the ERF components. Output torque and resistive torque are easily regulated.

The ERF brake and actuator devices of the present invention are particularly useful as a brake and actuator for an orthotic device. An orthotic device or orthosis is an externally worn device that applies a force to the body, usually across a joint, such as the knee or elbow. These forces are used to support, control, correct, or recover from any problems with the area of the body where the device is worn. An orthotic device in the form of a knee brace employing an ERF brake or actuator device 312 of the present invention is shown in FIGS. 19-21A. The orthotic device includes a support frame 314 attachable to the limb and hinged on both sides at the knee. An ERF brake or actuator device is mounted at the hinge assembly 316 on either one side or both sides. The ERF-based device may be solely a resistive element or may alternatively also provide torque generation, depending on the desired application. A gearbox 318 associated with each ERF brake or actuator device provides the interface between the ERF brake or actuator device 312 and the hinge 316. The ERF brake or actuator device can be modular, so the orthotic device can be switched between a resistive-only configuration to a platform including torque generation merely by switching the brake or actuator device.

The support frame 314 includes an upper frame 322 and a lower frame 324 connected by the hinge assembly 316. The hinge assembly may, for example, include a rotatable element 317 attached to the upper frame and a rotatable element 319 attached to the lower frame coupled together via an element 321. See FIG. 21B. Each frame is attachable to a limb, one above the joint and one below the joint. The frame may be constructed, for example, of a metal such as aluminum or a strong plastic or composite material such as a carbon fiber composite. The frame can be attached to the limb in any suitable manner that prevents the frame from shifting on the limb. For example, straps 326 that wrap about the limb may include hook and loop fasteners and may be padded with foam to conform to the patient's limb. The hinge assembly between the upper and lower frames is preferably the same on both sides of the brace. This allows the same orthotic device to be used on either the left or the right limb. Force is transmitted from the wearer through the straps and frame and leads to a torque at the hinge assembly.

Figure 22:
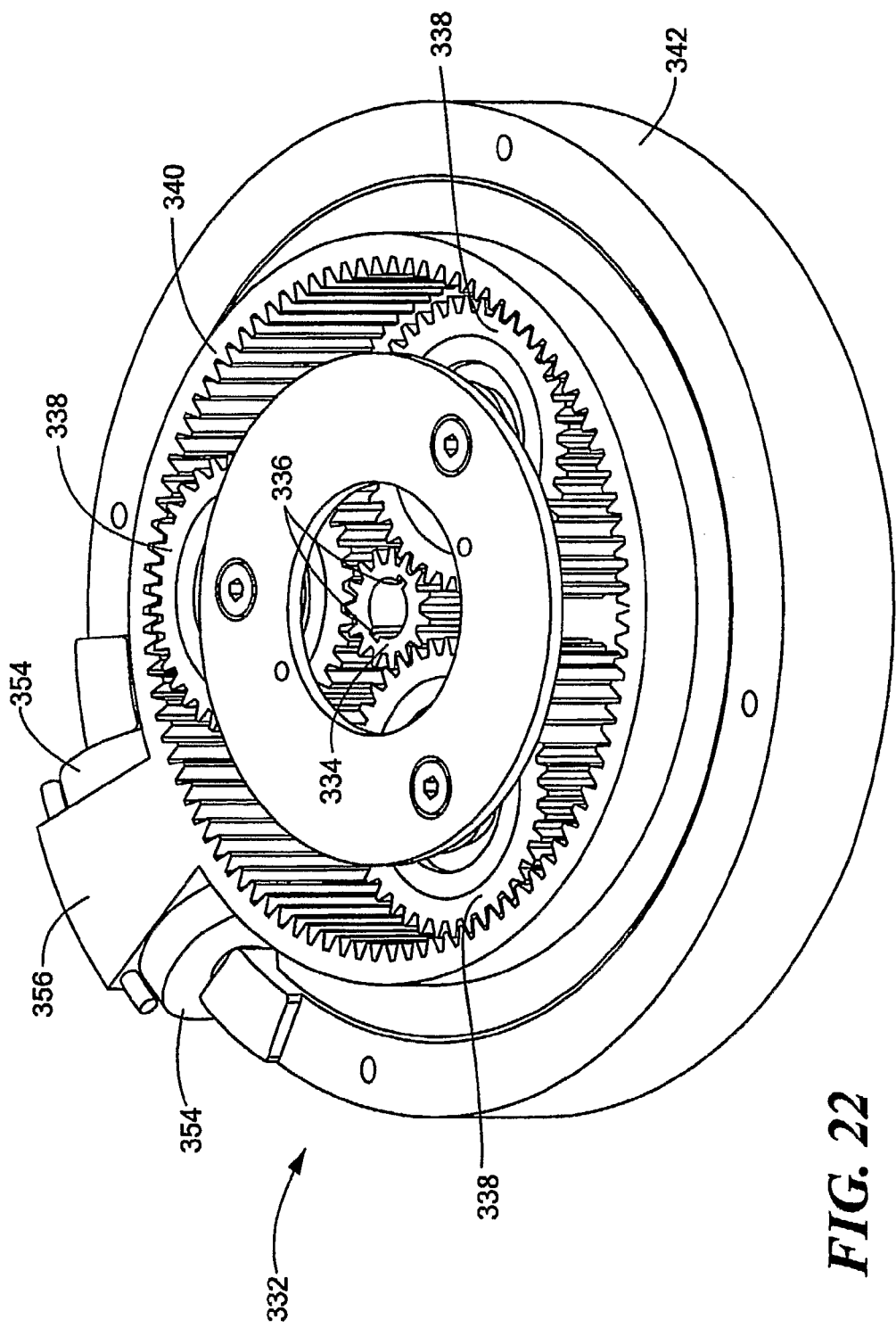
FIG. 22 is an isometric view of a gear assembly for use in the orthotic brace of FIG. 19.
Figure 23:
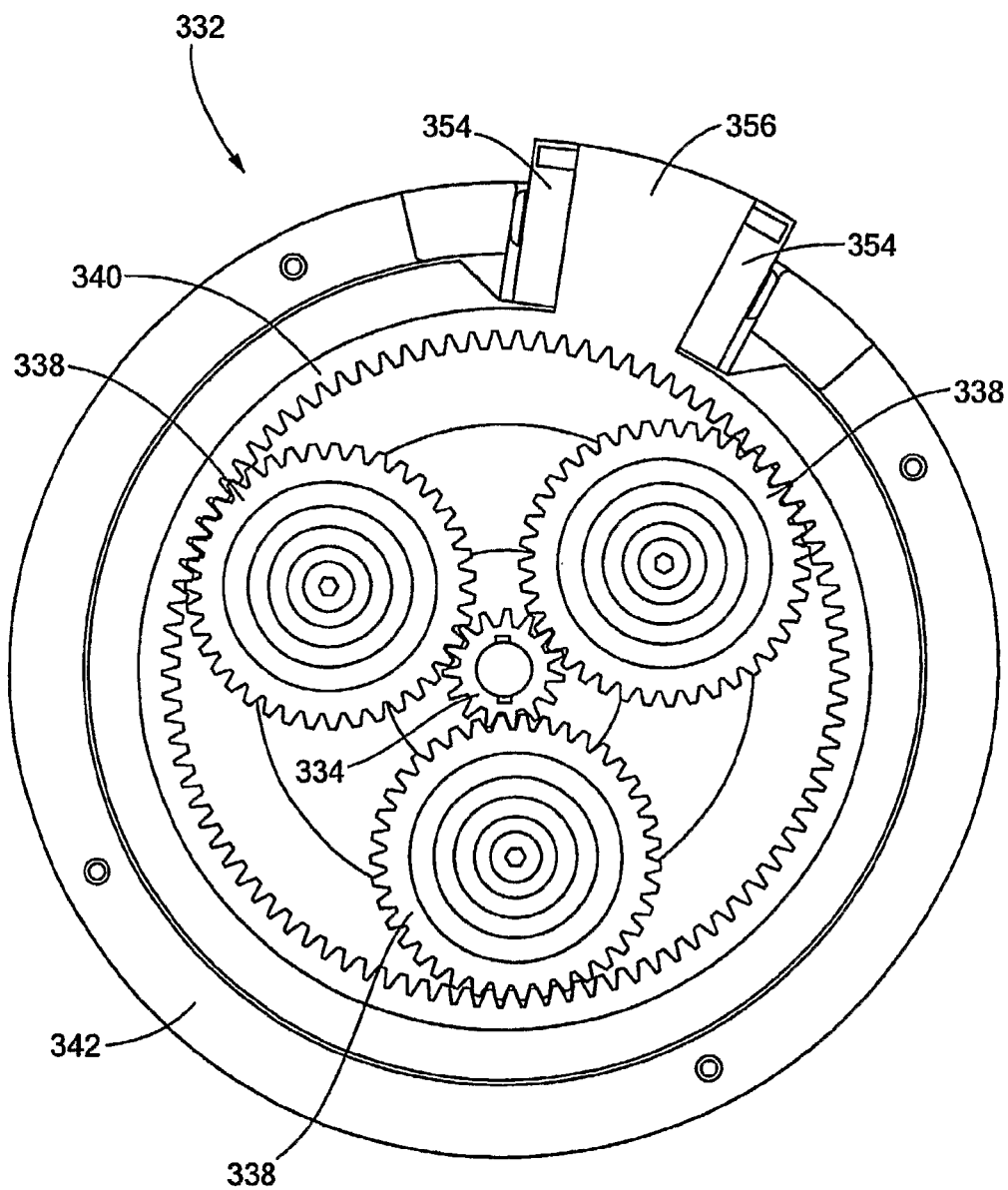
FIG. 23 is a top plan view of the gear assembly of FIG. 22.
Figure 24:
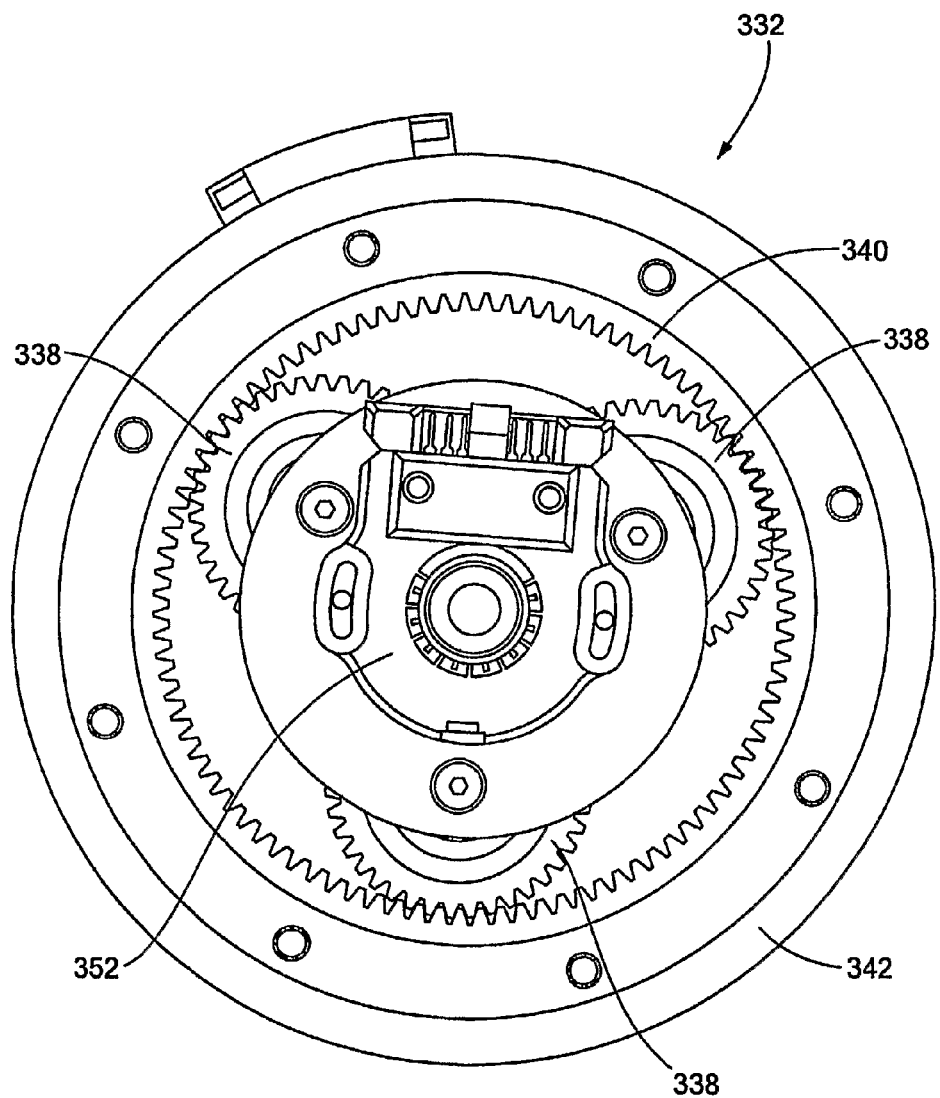
FIG. 24 is a bottom plan view of the gear assembly of FIG. 22.
Figure 25:
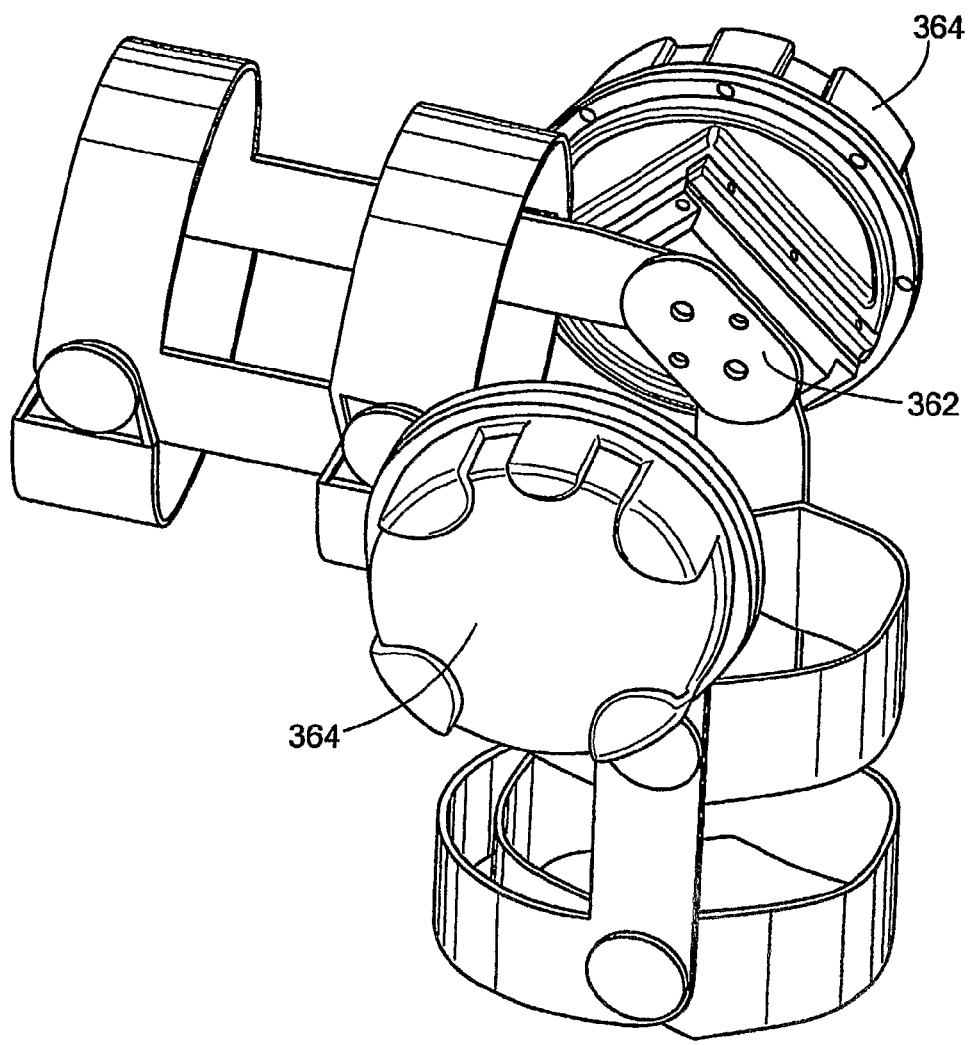
FIG. 25 is a further embodiment of an orthotic device for a leg incorporating two brake or damper devices or two actuator devices of the present invention.

The gearbox 318 transmits and multiplies the torque output of the brake or actuator device. The input/output shaft 330 of the ERF brake or actuator device connects to a gear assembly 332 within the gearbox. In the embodiment illustrated, the generated torque is multiplied using a planetary gear system that is contained in the hinge assembly 316. See FIGS. 22-24. In one exemplary embodiment, the torque is multiplied by 6.2:1. The shaft 330 connects to a pinion gear 334 via a pair of keyways 336. The pinion gear meshes with three planet gears 338, surrounded by a ring gear 340 fixed to a grounding ring or frame 342. The grounding ring is attached to the hinge assembly 316 to rotate therewith. The gearbox includes a suitable housing. The gearbox also serves as a mount for the brake or actuator device and as a hinge stabilizer.

The gearbox system also serves as a platform for the sensor system. Three sensors or sensor assemblies are preferably implemented in the device. The first sensor assembly measures angle, velocity, and acceleration of the knee and can be used for closed-loop control of the ERF brake or actuator device. An optical encoder 352, such as a standard rotary absolute optical encoder, or a Hall effect sensor, can be used. The second sensor assembly is a torque sensor for measuring the torque developed by the patient and also for closed-loop control of the ERF brake or actuator device. In the embodiment shown, two miniature compressor sensors 354 are arranged between an extension 356 of the ring gear 340 and the grounding ring 342 in opposite directions to measure torque via a force from a moment arm in both flexion and extension. When a torque is supplied to the hinge, the ring gear extension pushes on one of the sensors, depending on the direction of motion. This force measure is combined with known dimensional values (distance from the shaft to the sensor) to calculate the torque. Alternatively, force sensors can include strain gauges that are mounted onto the frame to measure the strain applied to the lower frame, which can be modeled as a simple beam. Torque can be subsequently calculated. Alternatively, torque sensors can be integrated into the hinge joint to directly measure the applied torque. In a further alternative, pressure sensors can be attached to the straps and, based on the given area, the force and torque can be calculated.

The third sensor assembly (not shown) is an array of force sensing resistors to monitor the interaction between the foot and the ground. The array can be integrated in an ankle-foot attachment that can be added to the knee brace for stroke patients in order to provide medio-lateral stability as in hinged ankle-foot orthosis. In healthy patients, the array can be located in an insole that patients wear in their shoes. The array allows the tracking of antero-posterior movements of the center of pressure and thus the ability to identify different phases of the gait cycle. This ability allows the implementation of control strategies for the knee orthosis.

Figure 26A:
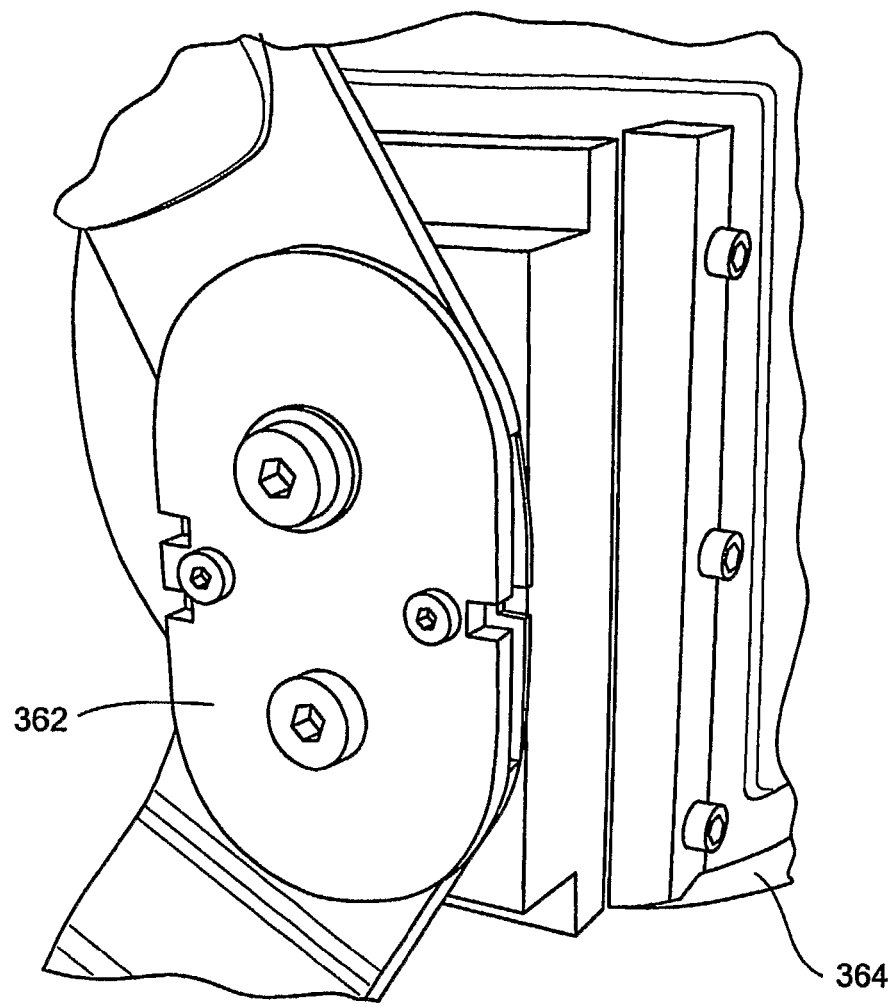
FIG. 26A is a partial view of a hinge assembly of the orthotic device of FIG. 25.
Figure 26B:
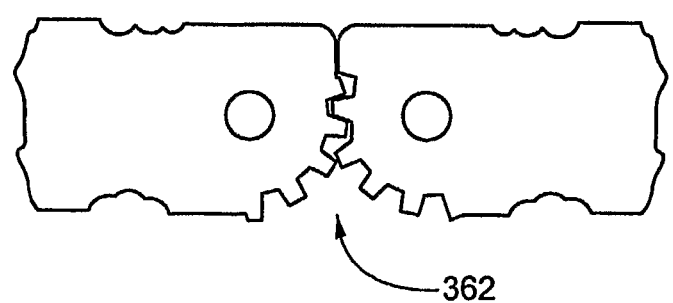
FIG. 26B is a schematic view of the hinge assembly of FIG. 26A.

In another embodiment, a polycentric hinge mechanism 362 can be used. See FIGS. 26A and 26B. The hinge mechanism includes upper and lower intermeshing elliptical gears. The elliptical gears produce an eccentric motion that lends itself to following the natural motion of the human knee. The input/output shaft of the ERF brake or actuator device 364 is attached to one of the gears.

The on-board electronics for the orthotic device include data acquisition from the sensors, computer logic, and actuation signals for the ERF brake or actuator device. The electronics are powered in any suitable manner, such as by batteries contained within a small handheld device. Flash memory can be used to store operating software and to record patient data. Wireless communication, such as via WI-FI, can be implemented to allow untethered use of the device. Visual outputs can be included to facilitate the use of the device, for example, by providing real-time display of joint angle and torque.

Figure 27:
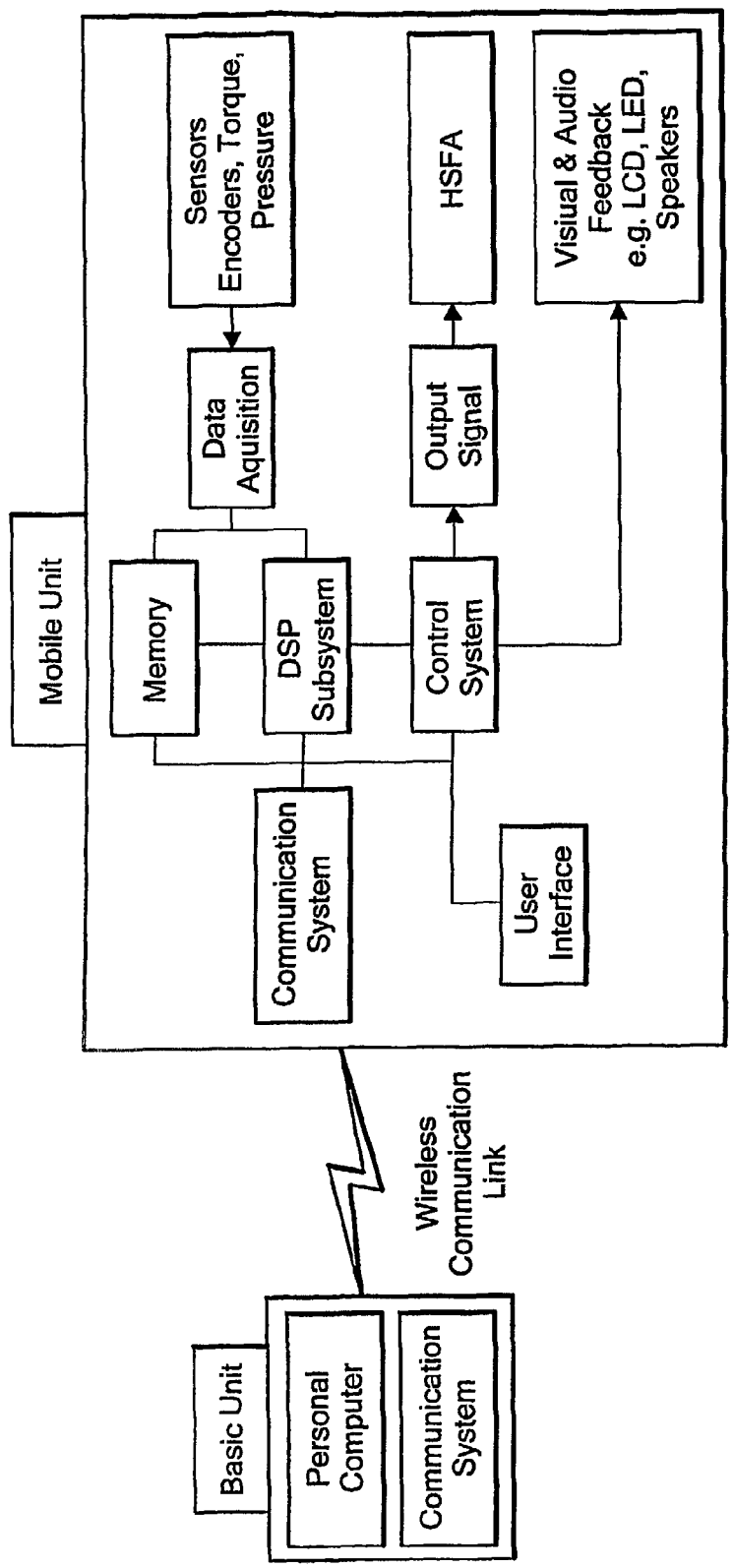
FIG. 27 is a diagram of a control system for an orthotic device of the present invention.

FIG. 27 shows a schematic representation of the electronics. The wireless communication link allows untethered collection of data from the board. It also allows the dynamic programming of the onboard controller. The system is able to operate in a stand-alone mode as well as in data coupling to a personal computer. The wireless frequency band can be in the range of 2.4 to 2.5 GHz, which is called the ISM band for Industrial, Scientific and Medical purposes. It can span more than 50 meters, transmitting a maximum un-coded data rate of 625 kbits/s. The transceiver module for the link is small in size with low power consumption. The on-board user interface allows the user to select a specific control mode without going to the computer. The device can include a recording capability to track its usage. The data can be downloaded remotely from the device and analyzed by a physician or physical therapist without the patient needing to revisit the medical facility.

Using an ERF brake or actuator device of the present invention, an orthotic device is capable of real time functionality. The device is readily controllable due to the field-dependant torque outputs and can react on the order of milliseconds. With such controllability, a rehabilitation regime can be tailored to each patient's individual needs. With closed loop control, feedback from the sensors allows a computer to calculate the efficiency of each specific exercise and alter the exercise in real time accordingly to achieve optimal levels of rehabilitation.

The power supply for the on-board electronics system can be, for example, a lithium-ion battery such as for a laptop. The ERF brake or actuator power should, however, be a separate system and can be the limiting factor in the battery life of the device. Nickel metal hydride batteries with 3000 to 4000 mAh and 24 V weigh approximately 500 to 600 g and allow the ERF brake device to run continuously at maximum capacity for 1.5 to 2 hours. With normal operation of the device, the battery life is estimated to be at least 4 to 5 hours. These batteries come in a wide selection of shapes and sizes, including AA, C, and D battery sizes as well as small block shapes. A 500 g pack of 20 AA size nickel metal hydride batteries is a representative cluster of the power supply necessary for several hours of actuation. The batteries can be located in the device or can be placed in a pack worn, for example, on a belt.

ERF power amplifiers are highly specialized, and standard off-the-shelf solutions are typically not suitable as they are not capable of the required fast response. ERF systems often demand a band-width in excess of 1 kHz. Recent technological improvements in the area of transformer core materials and low resistance MOSFET transistors, however, allow designs that are significantly smaller and higher in efficiency than previously available high voltage power supplies. Various micro-controller based switch mode power systems that are capable of producing high power outputs while maintaining a small mechanical footprint and low weight are now commercially available, such as from Smart Technology Ltd. These systems are specifically designed for the control of ERFs, and they can be customized for the requirements of an orthotic device, as can be readily determined by one of skill in the art. Customization entails providing the smallest solution for the power requirements of the device and using an enclosure of optimum shape.

Since the ERF brake and actuator devices are used in devices that are worn or operated by a human, safety is a consideration. A multiple concentric cylinder ERF brake device as currently designed with the ERF LID 3354S can operate with an estimated maximum 5000 volts DC at 1 mA of current. The low-current and low-power characteristics are within the safe operation margins of a device operated by a human even if the required voltage is high. All brake and actuator components are enclosed within a grounded metal enclosure to prevent accidental contact. Additionally, all high voltage wiring, switches, and metal parts have sufficient insulation and are inaccessible to the operator. A fast acting emergency cut-out is provided, which operates if the current rises above the rated maximum current and reduces the voltage to zero, as would be known in the art. To further prevent injury, the brake and actuator devices and the associated devices or mechanisms do not have any metal contact with the user and all electrically active components are insulated with materials that have high dielectric constants. Leakage of the ERF is minimized or prevented by utilizing spring-loaded Teflon seals, which have exceptional wear characteristics. The seals self-adjust as they wear down providing consistent performance for extended periods of use. Leakage between the lid and case is prevented with the use of an O-ring. If any of the seals should fail, ERF is non-toxic and cleans up with standard soaps and cleaners.

The orthotic device is compact and portable and is a wearable form of rehabilitation. A user can use the orthotic device in an average chair, while standing, or even during ambulatory motion. Use of the device is limited only by the user's abilities. Thus, weaker patients can use it for resistive exercises and stronger patients can use it for both weight training and proper gait training. Users can take the device with them to exercise on their own time, at home or work, or during their every day routines.

Additionally, aspects of the orthotic device of the present invention can be used with other brake devices or actuator devices, such as DC motors, magneto-rheological fluid brake devices, frictional brake devices, electropneumatic actuators, electromagnetic brake devices, hysterisis brake devices, eddy-current brake devices, pneumatic actuator devices, hydraulic actuator devices, voice-coil actuator devices, electro-active polymer actuator devices, ultrasonic motors and piezoelectric actuator devices according to principles well-known to those of skill in the art, given the guidance provided herein.

Figure 28:
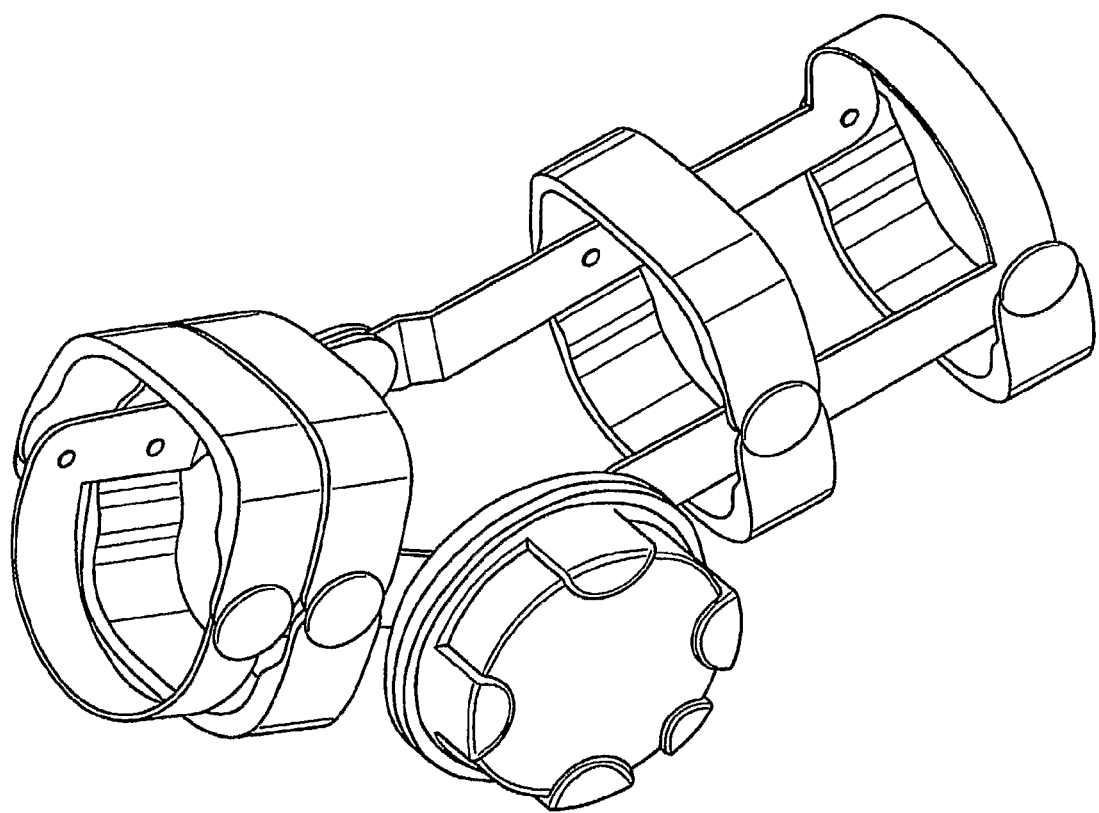
FIG. 28 is an isometric view of an orthotic device for an elbow incorporating a brake or damper device or an actuator device of the present invention.

Although described with particularity in conjunction with the knee, the orthotic device of the present invention can be used with any joint of the body, such as the elbow. See FIG. 28. A full or partial body suit can be assembled using the orthotic joints, which may have application in virtual reality, reducing muscle fatigue or enhancing muscle movement, and in microgravity compensation (such as assisting in reducing muscle and bone depletion on extended space visits).

The invention is not to be limited by what has been particularly shown and described, except as indicated by the appended claims.

What is claimed is:

1. An electro-rheological fluid actuator for generating a torque or force output and for providing resistance to a torque or force input, comprising:
   a housing comprising an insulative case, an input/output shaft rotatably mounted in the case;
   a plurality of rotatable members disposed arcuately within the case and coupled to the shaft;
   a plurality of rotatable electrodes formed as segments of a cylinder, each electrode mounted to an associated rotatable member for rotation therewith;
   a cylindrical ground electrode fixed to the case and concentric with the rotatable electrodes, a gap disposed between the ground electrode and the rotatable electrodes;
   an electro-rheological fluid disposed within the gap; and
   a plurality of linear actuator elements disposed within and motively coupled to an associated rotatable member to actuate rotation of the associated rotatable member.

2. The actuator of claim 1, wherein the linear actuators are operative sequentially to provide stepwise rotation of the rotatable members.

3. The actuator of claim 1, wherein the linear actuators are operative in conjunction with the rotatable electrodes, wherein rotation of a portion of the electrodes is locked by activation of the electro-rheological fluid and rotation of one rotatable electrode is permitted to provide stepwise rotation of the rotatable members.

4. The actuator of claim 1, wherein the electro-rheological fluid is activatable to provide resistance to an input torque on the shaft via a shear stress on the rotatable electrodes.

5. The actuator of claim 1, further comprising a plurality of rolling contacts operative to bring power to the rotatable electrodes, to the ground electrode, and to the linear actuators.

6. The actuator of claim 5, wherein the rolling contacts are aligned on an axle extending radially from the shaft, the rolling contacts rollable over contacts on a surface of the rotatable members.

7. The actuator of claim 1, further comprising a ratcheting mechanism operative to control direction of rotation of the linear actuator elements.

8. The actuator of claim 7, wherein the ratcheting mechanism includes a ratchet gear attached to the shaft, the ratchet gear having two rows of opposed teeth, and a ratchet cam operative to engage one row of teeth in a clockwise mode and another row of teeth in a counterclockwise mode.

9. The actuator of claim 8, wherein the ratcheting mechanism is operative in a neutral free-wheeling mode.

10. The actuator of claim 8, wherein the ratchet cam is mounted for pivoting motion by an elastic shaft, the elastic shaft mounted in a cam follower element to cause pivoting of the ratchet cam.

11. The actuator of claim 8, wherein the cam follower element is operative to travel a sinusoidal path activated by an external element to adjust the direction of rotation.

12. The actuator of claim 1, wherein the linear actuator elements comprise electromagnets.

13. The actuator of claim 1, wherein the linear actuator elements comprise solenoids.

14. The actuator of claim 1, wherein the linear actuator elements comprise piezoelectric actuators.

15. The actuator of claim 1, wherein the linear actuator elements comprise electro-active polymers.

16. An orthotic device for a joint comprising:
 a frame removably fixable to a limb of a user, the frame comprising a hinge assembly disposable at a joint of the limb;
 the electro-rheological actuator of claim 1; and
 a gear assembly attached to the shaft of the electro-rheological fluid actuator to couple an input or output force or torque to the hinge assembly.

17. The orthotic device of claim 16, wherein the device comprises a knee brace and the frame is configured for attachment to a leg.

18. The orthotic device of claim 16, wherein the device comprises an elbow brace and the frame is configured for attachment to an arm.

19. The orthotic device of claim 16, further comprising a sensor system comprising a sensor assembly operative to measure angle, velocity, and acceleration of the joint.

20. The orthotic device of claim 19, wherein the sensor assembly is operative to provide closed-loop control of the device.

21. The orthotic device of claim 16, further comprising a sensor system comprising a sensor assembly operative to measure torque on the shaft.

22. The orthotic device of claim 21, wherein the sensor assembly is operative to provide closed-loop control of the device.

23. The orthotic device of claim 16, further comprising a second electro-rheological fluid device disposed on an opposite side of the joint.

24. The orthotic device of claim 16, further comprising a controller assembly operative to control the electro-rheological fluid device.

25. The orthotic device of claim 24, wherein the control assembly is operative to provide remote communication.

26. The orthotic device of claim 16, wherein the device is operable under battery power.

27. The orthotic device of claim 26, wherein one or more batteries are disposed within the device.

28. The orthotic device of claim 26, wherein one or more batteries are disposed externally to the device.

\* \* \* \* \*